United States Patent
Mack et al.

(10) Patent No.: US 7,785,257 B2
(45) Date of Patent: Aug. 31, 2010

(54) SYSTEM AND PROCESS FOR NON-INVASIVE COLLECTION AND ANALYSIS OF PHYSIOLOGICAL SIGNALS

(75) Inventors: David C. Mack, Charlottesville, VA (US); Steven W. Kell, Keswick, VA (US); Majd Alwan, Charlottesville, VA (US); Robin Felder, Charlottesville, VA (US); Beverly Turner, North Garden, VA (US); Sarah Wood, Lovingston, VA (US)

(73) Assignee: Home Guardian LLC, Charlottesville, VA (US)

( * ) Notice: Subject to any disclaimer, the term of this patent is extended or adjusted under 35 U.S.C. 154(b) by 107 days.

(21) Appl. No.: 12/168,413

(22) Filed: Jul. 7, 2008

(65) Prior Publication Data
US 2008/0275314 A1  Nov. 6, 2008

Related U.S. Application Data

(63) Continuation of application No. 10/974,027, filed on Oct. 27, 2004, now Pat. No. 7,396,331.

(60) Provisional application No. 60/514,677, filed on Oct. 27, 2003.

(51) Int. Cl.
*A61B 5/00* (2006.01)

(52) U.S. Cl. .................. 600/300; 600/481; 600/508; 600/529

(58) Field of Classification Search .............. 600/300, 600/481–543
See application file for complete search history.

(56) References Cited

U.S. PATENT DOCUMENTS

| 4,085,740 | A | * | 4/1978 | Allen, Jr. .................. 600/500 |
| 4,163,447 | A |   | 8/1979 | Orr |
| 4,306,657 | A |   | 12/1981 | Levy |
| 4,444,199 | A |   | 4/1984 | Shafer |
| 4,784,162 | A | * | 11/1988 | Ricks et al. .............. 600/484 |
| 4,889,123 | A |   | 12/1989 | Lee |
| 4,958,638 | A | * | 9/1990 | Sharpe et al. ............ 600/407 |
| 4,989,002 | A | * | 1/1991 | Tan .......................... 341/120 |
| 5,291,013 | A | * | 3/1994 | Nafarrate et al. ....... 250/227.14 |

(Continued)

OTHER PUBLICATIONS

"Non-Invasive Analysis of Physiological Signals (NAPS): A Low Cost, Passive Monitor for Sleep Quality and Related Applications," D. Mack, S. Kell, M. Alwan, B. Turner, M. Wolfe, R. Felder, and T. Skalak, Poster Paper, CBI Steps to Success Conference, Roanoke, VA, Oct. 5, 2002.

(Continued)

*Primary Examiner*—Patricia C Mallari
*Assistant Examiner*—Karen E Toth
(74) *Attorney, Agent, or Firm*—Townsend and Townsend and Crew LLP

(57) ABSTRACT

A system and method for detecting, monitoring and analyzing physiological characteristics. Signals from a subject are acquired from a suite of sensors, such as temperature, carbon dioxide, humidity, light, movement, electromagnetic and vibration sensors, in a passive, non-invasive manner. The signals are processed and physiological characteristics are isolated for analysis. The system and method are to analyze sleep patterns, as well as to prevent bed sores or detect conditions such as illness, restless leg syndrome, periodic leg movement, sleep walking, or sleep apnea. However, numerous other applications of the invention are also disclosed.

20 Claims, 19 Drawing Sheets

U.S. PATENT DOCUMENTS

| | | | |
|---|---|---|---|
| 5,295,490 | A | 3/1994 | Dodakian |
| 5,335,657 | A | 8/1994 | Terry, Jr. et al. |
| 5,590,650 | A | 1/1997 | Genova |
| 5,891,023 | A | 4/1999 | Lynn |
| 5,902,250 | A | 5/1999 | Verrier et al. |
| 6,223,064 | B1 | 4/2001 | Lynn et al. |
| 6,287,253 | B1 * | 9/2001 | Ortega et al. ............... 600/300 |
| 6,315,736 | B1 * | 11/2001 | Tsutsumi et al. ............ 600/500 |
| 6,342,039 | B1 | 1/2002 | Lynn et al. |
| 6,468,234 | B1 | 10/2002 | Van der Loos et al. |
| 6,485,441 | B2 | 11/2002 | Woodward |
| 6,491,642 | B1 | 12/2002 | Stasz |
| 6,506,153 | B1 | 1/2003 | Littek et al. |
| 6,719,708 | B1 * | 4/2004 | Jansen ........................ 600/587 |
| 6,749,548 | B2 | 6/2004 | Hoffman |
| 6,752,766 | B2 | 6/2004 | Kowallik et al. |
| 6,458,087 | B1 | 10/2004 | Al-Rasheed |
| 7,027,358 | B1 * | 4/2006 | Esposito et al. ............... 368/10 |
| 2003/0045806 | A1 * | 3/2003 | Brydon ....................... 600/534 |
| 2003/0139678 | A1 * | 7/2003 | Hoium et al. ............... 600/510 |
| 2005/0165284 | A1 * | 7/2005 | Gefen ........................ 600/300 |
| 2006/0063982 | A1 * | 3/2006 | Sullivan et al. ............. 600/301 |
| 2006/0241510 | A1 | 10/2006 | Halperin et al. |
| 2007/0083125 | A1 | 4/2007 | Ouchi et al. |

OTHER PUBLICATIONS

"Non-Invasive Analysis of Physiological Signals (NAPS): A Vibration Sensor that Passively Detects Heart and Respiration Rates as Part of a Sensor Suite for Medical Monitoring," David C. Mack, Steve W. Kell, Majd Alwan, Beverley Turner and Robin A. Felder, 2003 Summer Bioengineering Conference, Jun. 25-29, Sonesta Beach Resort in Key Biscayne, FL, Medical Automation Research Center, University of Virginia, Charlottesvile VA.

"A New Method for Long-Term Monitoring of the Ballistocardiogram, Heart Rate, and Respiration," J. Alihanka, K. Vaahthoranta and I. Saarikivi, Department of Physiology, University of Turku, 20520 Turku 52, Finland, 1981 the American Physiological Society.

"The Validity of the Static Charge Sensitive Bed in Detecting Obstructive Sleep Apnoeas," O. Polo, L. Brissaud, B. Sales, A. Besset, M. Billiard, *Eur Respir J.* 1988, 1, 330-336.

"Nightcap: A Home-Based Sleep Monitoring System," Adam Mamelak and J. Allan Hobson, *Sleep*, 12(2):157-166, Raven Press, Ltd., New York, 989 Association of Professional Sleep Societies, Oct. 1988.

"A Pressure-Sensitive Mat for Measuring Contact Pressure Distributions of Patients Lying on Hospital Beds," Charles F. Babbs, M.D., Ph.D., Joe D. Bourland, Ph.D., George P. Graber, James T. Jones, William E. Schoenlein, *Biomedical Instrumentation & Technology*, Oct. 1990.

"A Limited Diagnostic Investigation for Obstructive Sleep Apnea Syndrome, Oximetry and Static Charge Sensitive Bed," Eva Svanborg, M.D., Ph.D., Hakan Larsson, M.D., Britt Carlsson-Nordlander, M.D., Ph.D. And Ritva Pirskanen, M.D., *Chest*, 98/6/ Dec. 1990.

"Monitoring of the Ballistocardiogram with the Static Charge Sensitive Bed," Ben H. Jansen, Senior Member, IEEE, B. Hans Larson and Kris Shankar, 1991, The Institute of Electrical and Electronics Engineers, Inc.

"Sleep and Apnea in the Elderly: Reliability and Validity of 24-Hour Recordings in the Home," Christine Acebo, Robert K. Watson, Linda Bakos, and Evelyn B. Thoman, *Sleep*, 1991 American Sleep Disorders Association.

"Technology and Equipment Review, Portable Sleep Screening Systems," *Journal of Clinical Neurophysiology*, 91:154-159, Raven Press, Ltd., New York, 1992 American Electroencephalographic Society.

"Sleep Staging with Movement-Related Signals," Ben H. Jansen and Kris Shankar, *Int J. Biomed Comput*, 32 (1993) 289-297 1993 Elsevier Scientific Publishers Ireland Ltd.

"Development of Sleep Position Monitor," H. Baker, M.A. Corrales, A. Meza, A.R. Zapata, *Med. & Biol. Eng. & Comput.*, 1995, 33, 112-114.

"Fully Automated Health Monitoring System in the Home," Toshiyo Tamura, Tatsuo Togawa, Mitsuhiro Ogawa, Mikiko Yoda, *Medical Engineering & Physics*, 1998 IPEM, Published by Elsevier Science Ltd.

"Assessment of Bed Temperature Monitoring for Detecting Body Movement During Sleep: Comparison with Simultaneous Video Image Recording and Actigraphy," T. Tamura, S. Miyasako, M. Ogawa, T. Togawa, T. Fujimoto, *Medical Engineering & Physics* 1999 IPEM, Published by Elsevier Science Ltd.

"Unconstrained Physiological Monotoring in Daily Living for Health Care," Ken-Ichi Yamakoshi, *Frontiers Med. Biol. Engng.*, vol. 10, No. 3, 239-259 (2000).

"Estimation of Bed-Ridden Human's Gross and Slight Movement Based on Pressure Sensors Distribution Bed," Tatsuya Harada, Tomomasa Sato and Taketoshi Mori, Oct. 2002, The University of Tokyo 7-3-1 Bunkyo-ku Hongo, Tokyo 113-8656 Japan; 2002 IEEE International Conference on Intelligence Robots and Systems.

"A bed temperature monitoring system for assessing body movement during sleep," T. Tamura, T. Togawa and M. Murata, *Clin. Phys. Physiol. Meas.*, 1988. vol. 9., No. 2, 139-145, Great Britain.

\* cited by examiner

SYSTEM AND PROCESS FOR NON-INVASIVE COLLECTION AND ANALYSIS OF PHYSIOLOGICAL SIGNALS

CROSS-REFERENCES TO RELATED APPLICATIONS

This application is a continuation of and claims the benefit of U.S. patent application Ser. No. 10/974,027 filed Oct. 27, 2004, which claims the benefit of U.S. Provisional Application No. 60/514,677, filed Oct. 27, 2003, the contents of which are incorporated by reference herein in their entirety.

FIELD OF THE INVENTION

The invention relates to non-invasive analysis of physiological signals and more particularly to a system and process for detecting, collecting and processing physiological characteristics acquired by a suite of sensors embedded in a person's environment.

BACKGROUND OF THE INVENTION

There are large amount of people affected by sleep related conditions who could benefit from knowing more about their sleep habits. Some research indicates that 40% of all American adults suffer from some kind of sleep disorder, while about 70 million Americans are chronically sleep deprived. Many feel that little substantial improvement can be made to correct their problems, since sufferers often do not discuss the problem with their physician.

The current gold standard for sleep research is known as polysomnography (PSG), which involves at least the recording of an electroencephalogram (EEG), a measurement of brain waves, an electrooculogram (EOG), a measurement of muscle activity in the eye area, and an electromyogram (EMG), a measurement of muscle activity in specific areas such as the arm or leg. These waveforms allow a doctor to assess a patient's sleep quality. All of these electrode hook-ups prove valuable in obtaining relevant information used to assess sleep quality, but require patients to have electrodes attached to their bodies.

In an effort to provide a less intrusive way to study sleep on a longer-term basis, actigraphs have been developed. These devices can be attached to any of the limbs and provide movement data based on the same principles behind accelerometers. They are also used in activity studies and can provide twenty-four hour monitoring of the subject. This type of sensor, however, has its limitations in acquiring data that can be interpreted definitively to provide a good assessment of sleep quality. Researchers are dependent on patient journals to help correlate the data recorded on the actigraph and it is hard to distinguish different events that can occur throughout the night. Patient non-compliance in journaling adds to the confusion. In addition, many of the problems researchers have interpreting results from actigraphs are a direct result of the one-dimensional nature of the data recorded. For example, if a patient places their hand on their chest or under their head, the motion data recorded by the actigraph can be misinterpreted or could potentially hide important events.

To provide an even less intrusive approach that does not involve equipment attached to the subject, different physiological parameters must be examined. One way to look at cardiologic and respiratory events is through a technique called ballistocardiography (BCG). BCG involves the study of the cardiac system by measuring forces related to the contraction and relaxation of the heart, along with forces propagated throughout the vascular system. It has been shown that cardiac forces correlate to life duration and susceptibility to ischemic heart disease. Additionally, it has been shown that the average force seen in the BCG reduces as a person ages. Unfortunately, initial high expectations and hopes set forth in the mid-20th century for this technology simply resulted in disappointments because inadequate analysis tools were available. In addition, the electrocardiogram (ECG) quickly usurped this technology as a more practical way to measure cardiac function.

Now that data acquisition systems are commonplace and the cost of personal computers have been greatly reduced in the last decade, analysis of the BCG data is no longer an insurmountable hurdle. In fact, a team from Stanford University designed a system called "SleepSmart" that uses an array of pressure and temperature sensors to acquire physiological data. These sensors are embedded in a mattress and can detect position, temperature, sound, vibration and movement, with other sensors optional for additional information. They determined that a sheet of piezoelectric film was best for implementation of their design. However, they were only able to obtain results similar to a static charge sensitive bed in that they were able to obtain good measures of breathing waveforms, but unable to obtain reliable heart rate measures, thus deeming the technology insufficient for medical application.

Previous efforts to passively, i.e., without the active involvement of the subject and without direct connection of sensors to the subject, collect physiological data have been expensive, as processing ability for analysis sufficient for medical applications was inefficient and expensive. Isolating the appropriate components from a signal required complicated circuitry and processing. This complexity added expense without a proportional increase in accuracy and reliability of the outputs. Due to the number of people that suffer from sleep related disorders, as well as the need for non-invasive collection of medical and other data in applications such as, monitoring the conditions of sick, old or bedridden patients and prenatal infants, there is need for a more efficient and accurate passive data collection and analysis system to monitor various conditions of subjects. In particular, there is a need for such a passive system in hospitals, nursing homes, assisted living facilities, sleep labs or home sleep study centers, doctors' offices, health monitoring stations and the like.

BRIEF SUMMARY OF THE INVENTION

The invention avoids the disadvantages and drawbacks of the prior art and/or satisfies the need for more efficient and accurate passive data collection and analysis by providing for improved passive data collection, signal processing and analysis of the psychological characteristics. In particular, the invention satisfies this need by providing a system and method employing a network of sensors at least some of which passively detect physiological characteristics of the subject. The output from the network of sensors is processed in a novel manner using a series of signal filters to isolate signals for the desired physiological characteristics such as heart rate and breathing rate. The physiological characteristics are then analyzed for research and/or diagnosis.

The invention thus provides improved signal processing while increasing efficiency without adding exorbitant costs. The processing is computationally and cost effective, thereby allowing a more comprehensive analysis of physiological characteristics of a subject. Further, opportunities for studies and/or diagnostics to be performed on subjects are increased due to the improved, cost effective signal processing.

The invention may be implemented in a number of ways. According to one aspect of the invention a non-invasive system for assessing physiological characteristics of a subject, is provided. The system includes a network of sensors configured to provide electronic output signals indicative of at least one sensed condition. The network includes at least one passive sensor selected from the group consistently of vibration, temperature, carbon dioxide, light and electromagnetic sensors. Data acquisition circuitry may be provided for collecting the electronic signals output from the network of sensors. A processor is configured to process the electronic signals and includes an amplifier configured to amplify at least one of the electronic signals, and first and second filters configured to receive the amplified electronic signals to produce two processed electronic signals. The first filter may include a band pass filter and the second filter may include a low pass filter and a high pass filter. An output device may also be provided for outputting the processed signals into human-readable data indicative of at least one condition of a subject.

According to a further aspect of the invention, the system includes an array of ultra-sensitive sensors capable of detecting movements induced by cardiac and respiratory forces, and is particularly adapted to assess the quality of sleep of a subject. The human-readable data comprises at least one of a heart rate waveform and a respiratory waveform, an obstructive sleep apnea count, and a subject movement percentage.

According to an additional aspect of the invention, at least one sensor may be formed from a matrix of momentary binary pressure-sensitive contact switches that are embedded in a mattress pad, block of foam, bed sheet, or a chair, said matrix providing electronic signals corresponding to a positional map of the subject.

According to a further exemplary aspect of the invention, a method of analyzing physiological characteristics of a subject including cardiac and/or respiratory parameters on a beat-by-beat or breath-by-breath basis is provided. The method may include various steps including passively detecting physiological characteristics through a network of sensors requiring no conscious input by the subject and being capable of providing electronic output signals indicative of a sensed condition. At least one sensor may be selected from the group consisting of vibration, position, temperature, relative humidity, carbon dioxide, light and electromagnetic sensors. The electronic signals output from the network of sensors may be collected for processing. During the processing step, at least one of the electronic signals may be amplified and fed to first and second filters to produce two processed electronic signals. The first filter may include a band pass filter and the second filter may include a low pass filter and a high pass filter. Finally, the processed signals may be output into human-readable format, such as waveforms indicative of cardiac and/or respiratory conditions.

In addition to sleep data obtained in a bed or chair, the invention may be used for gathering general physiologic or neural parameters of a subject in a chair or bed while subjects are awake during their daily living activities. Such a system could provide important information. For example, measuring how quiet or active a subject is behaving in response to various external stimuli could give important clues as to physiologic reactivity, mood, or disposition. Physiologic responses to entertainment, socialization, and other mental or physical stimuli of any nature whether the stimuli is visual, tactile or audible could be important for assessing physical or mental health. General health assessments may be performed based on the physiologic responses. In addition, responses could give important clues as to how consumers behave in response to the aforementioned stimuli. Thus, the invention is applicable not only for gathering and interpreting data during sleep, or for diagnosing health conditions of sick people, but also for gathering and interpreting data related to normal human responses during all hours of wakefulness to external visual, tactile, audible stimuli, or other conditions.

Additional and alternative features, advantages, and embodiments of the invention are set forth or apparent in the following detailed description, drawings and claims. Although numerous implementations and examples of the invention are set forth—including in this "Summary of the Invention" section—the examples and implementations are not intended to limit the scope of the invention as claimed. While the invention was developed during research on, and is particularly adapted to analysis of sleep related conditions, it should be readily apparent that the invention may be used in a number of other applications such as pre-natal monitoring, determining surgery patient activity, movement of bedridden individuals and other applications that skilled artisans would recognize.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. In the drawings:

FIG. 12A is an EKG waveform, while

DETAILED DESCRIPTION OF THE INVENTION

Figure 1:
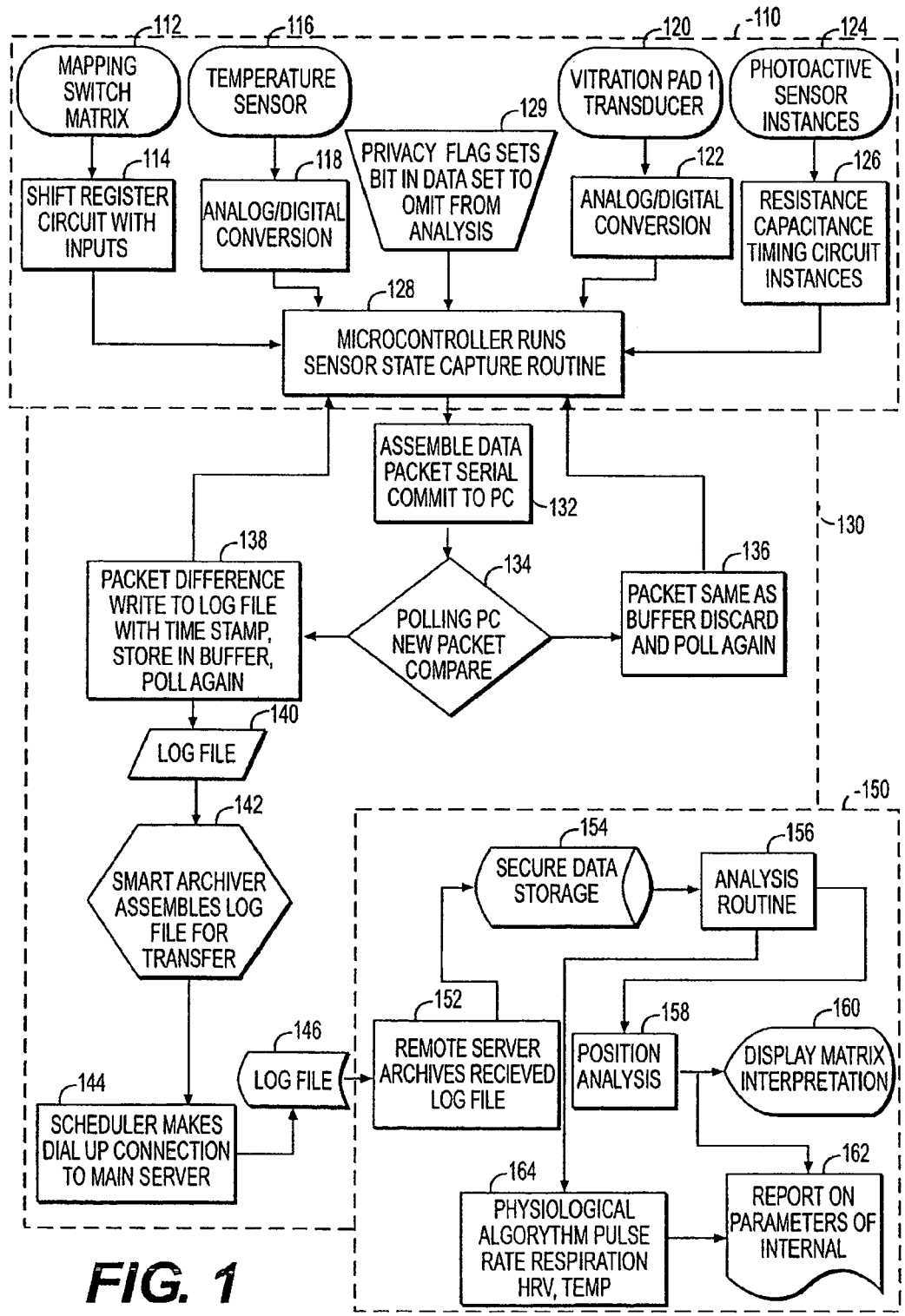
FIG. 1 is a flow chart schematically illustrating a first embodiment of a non-invasive, data acquisition and processing system constructed according to the principles of the invention.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law.

A method and system are provided whereby multiple types of sensors may be used to passively detect physiological characteristics of a subject, such as, for example, physiological characteristics associated with analyzing quality of sleep. Preferably, all of the sensors are passive sensors, which operate without any conscious input from or direct connection to the subject. The sensors are formed into one or more suites to provide more complete detection of numerous physiological characteristics. According to an exemplary embodiment of the invention, ultra-sensitive vibration sensors are used to provide, through signal processing techniques, waveforms of heart rate, breathing rate, snoring and other physiological characteristics. To work in the sleep environment of the invention, the vibration sensors must be sensitive enough to detect small movements of the body or body tissue generated by cardiac forces. More particularly, the voltage of the sensors may saturate when gross movement occurs, thereby allowing differentiation between gross movement and cardiac or respiratory events. These sensors may be piezoelectric, fiber optic, load cell based or other types of sensors of suitable sensitivity known in the art, such as piezoelectric air pressure sensors commercially available from Motorola and others. In concert with these sensors, temperature sensors, carbon dioxide sensors, light sensors, electromagnetic sensors and/or simple momentary contact switches may be provided to form a suite of sensors that provides multi-dimensional data about the user without the use of any type of camera or microphone equipment. The piezoelectric sensor, some of the temperature sensors and the momentary contact switches may be embedded in a mattress pad, while other sensors may be embedded in a pillow. Additional sensors may be located proximal to the bed, such as in a swing arm located above a bed. The sensors may be made compatible with any existing bed or other support structure.

Data from the sensors may be acquired through the use of a microcontroller/microprocessor module and the use of additional components, such as instrumentation amplifiers and filters. The sensors provide longitudinal sleep data (e.g., sleep data collected over one or more nights) to provide a better understanding of how, over an extended period of time, a person's sleep can be analyzed and evaluated to make improvements where necessary. In addition, this sensor suite may be adapted to fit other applications a skilled artisan would recognize besides measuring physiological parameters associated with analyzing quality of sleep such as monitoring physiological conditions in a chair (including wheelchairs), monitoring patients that are confined to intensive care unit hospital beds, monitoring children's vital statistics, such as those of premature babies, and detecting pressure points that could possibly develop into bedsores. Additionally, detection of illness, restless leg syndrome, periodic limb movement and sleepwalking may also be done. In addition, there may be applications where monitoring healthy people at rest or in other states may be beneficial. Various features and exemplary embodiments of the invention will now be described in more detail with reference to the figures below.

FIG. 1 is a flow chart schematically illustrating a first embodiment of a non-invasive data acquisition and processing system constructed according to the principles of the invention. While the data flow is described in a particular manner, it is understood that the data may flow and be processing in a variety of configurations, as recognized by skilled artisans. Generally, the flowchart may be broken into three circuitry sections: a module for data acquisition 110; a module for arranging data 130; and, a module for analyzing data 150.

Inputs from the suite of sensors detecting physiological conditions of a subject form part of the data acquisition module 110. Data acquisition module 110 includes a mapping switch matrix 112 that provides data to a shift register at 114. Data from the mapping switch matrix 112 includes data based on the position of the subject on a mattress, described in more detail below with reference to FIG. 2, or other support. The shift register 114 outputs the positional data to a micro-controller 128. One or more temperature sensors 116 provide temperature data to an analog-to-digital converter 118 that provides the output to micro-controller 128. By way of example, if the temperature sensor 116 is a digital sensor, the analog-to-digital converter 118 may be omitted.

Data acquisition module 110 further includes a vibration pad 120 that provides vibrational and movement data to an analog-to-digital converter 122, which provides its output to micro-controller 128. Vibration pad 120 may be an ultra-sensitive pressure transducer, such as a commercially available piezoelectric air pressure sensor for sensing respiratory and/or cardiac movement of a subject. Further, a photo-active sensor 124 provides data to a circuit 126, (i.e., resistance/capacitance timing circuit), which communicates with the data micro-controller 128. By way of example, if the photo-active sensor 124 is a digital sensor, the analog-to-digital circuit 126 may be omitted. The photo-active sensor 124 may sense the ambient light to determine the relative light, the time of day and the conditions of the subject.

Micro-controller 128 runs a sensor state capture program to capture the data from the various sensors at some set interval, with the exception of the vibration pad, and provide a log of that data. The vibration pad may be sampled continuously for a set amount of time, such as 5 or 10 seconds. The micro-controller 128 counts the peaks/troughs in the vibration pad signal with set limits for the maximum possible pulse and respiration rates, and calculates the pulse and respiration rate based on the count. The other data is sampled in between the runs of the time interval (e.g., the 5 or 10 second periods). The capture program involves sampling the switch matrix 112, the temperature sensor 116, the vibration pad 120 and the photo-active sensor 124 to see if there is additional data on a change in state. The data is pulled from the various sensors. Optionally, the switch matrix 112 could be run on an additional micro-controller 128 for more sensitive position and movement analysis.

A privacy flag 129 sets bits in the data set via a user operated switch to flag the data for omission from analysis. Thus, privacy maybe provided for the user when desired.

The micro-controller 128 provides the interface between the sensors and the processor, described below. The data acquisition module 110, in part through micro-controller 128, provides for addressing and synchronization, as well as adequate sampling of the signals coming from the sensors, which are converted from analog to digital format, if necessary.

In data arrangement module 130, data captured by the micro-controller is assembled and sent to a processor, such as a personal computer, at 132. The assembled data may be transmitted by packets or serially. Other manners of transmitting the data known in the art may also be used. The processor compares the new data from each sensor received at 134. If the new data received is the same as that is in a buffer, the data is discarded and the processor polls the micro-controller for additional data at 136. This may minimize the size of the recorded data set.

If the new sensor data is different from the old, the data is logged at 138. Logging the data may include writing the data to a log, recording a time stamp, and/or storing the information in a buffer. The processor may then poll the micro-controller 128 for additional data from one or more of the sensors. A log file is created at 140. The log file may contain information related to one or more sensors, changes in sensor data, and the time stamp. The log file may contain all such information since the last transmission of the log file, as described below. An archiver assembles the log file for transfer at step 142. According to an embodiment of the invention, data from the log file may be transferred at specified intervals (e.g, hourly, daily, weekly, etc.) or in conjunction with specified events (e.g., heart rate outside parameters, temperature indicating fever/flushing, etc.). A server is connected at 144. By way of example, a scheduler may establish a dial-up connection with the server. The log file is transferred at 146. The server may comprise a central location for accessing data obtained by data acquisition module 110.

In the data analysis module 150, the server receives and records the log file at 152. The data in the log file may be stored in a data storage device at 154, according to an embodiment of the invention. Due to the nature of the data, it may be desirable for the data to be stored in a secured storage.

At 156, an analysis routine is performed on the stored data. A positional analysis is performed at 158, which may include determining, based on the data, the position of the subject at various times during the gathering of the initial data. Based on the positional analysis, a display matrix is interpreted at 160, i.e., it may be output on a monitor or printed out. By way of example, the display matrix may be similar to that illustrated in FIGS. 4A, 4B, and 4C, below.

In the analysis module 150 information derived from each of the sensors may be interpreted to provide indications of the state of various physiological characteristics. These include, but are not limited to heart rate, HRV, blood pressure, respiratory rate and regularity, apneas and hypopneas, body surface temperature at multiple points, restlessness or activity levels, body position, as well as detailed movement information and pressure points. By way of example, skin temperature and/or pulse magnitude may be measured at the extremities, such as the lower leg or foot, and compared to the measurements of the upper body or torso to calculate a peripheral vascular resistance (PVR). PVR is a characteristic linked to the detection of cardiovascular disease. These results can be displayed through visual feedback, such as a monitor located remotely or at the apparatus itself, and/or as a summary report or graph on a personal computer. Thus, the positional analysis at 158 and/or physiological, algorithms pulse rate, restriction, heart rate variability (HRV) 164 and/or temperature values, etc., may be integrated into one or more reports at 162. The results may also be sent through a secure connection to a secure remote database that is accessible by the primary care provider of the individual or other necessary health professionals associated with the individual so as to provide them with this information.

The analysis routine thus may include a subroutine such as shown at 164 for determining various physiological characteristics such as those discussed above. According to one feature of the invention, one or more physiological algorithms may be used to determine the pulse or heart rate, the respiration rate, the HRV rate, and other physiological information. An example of an algorithm that may be used is discussed below in conjunction with FIG. 14. The physiological information may also be integrated into a report or graph at 162. The report may include the parameters on the subject for studying the physiological information about the subject. Physiological algorithm 164 analyzes the processed signals to generate desired waveforms and information.

Figure 2:
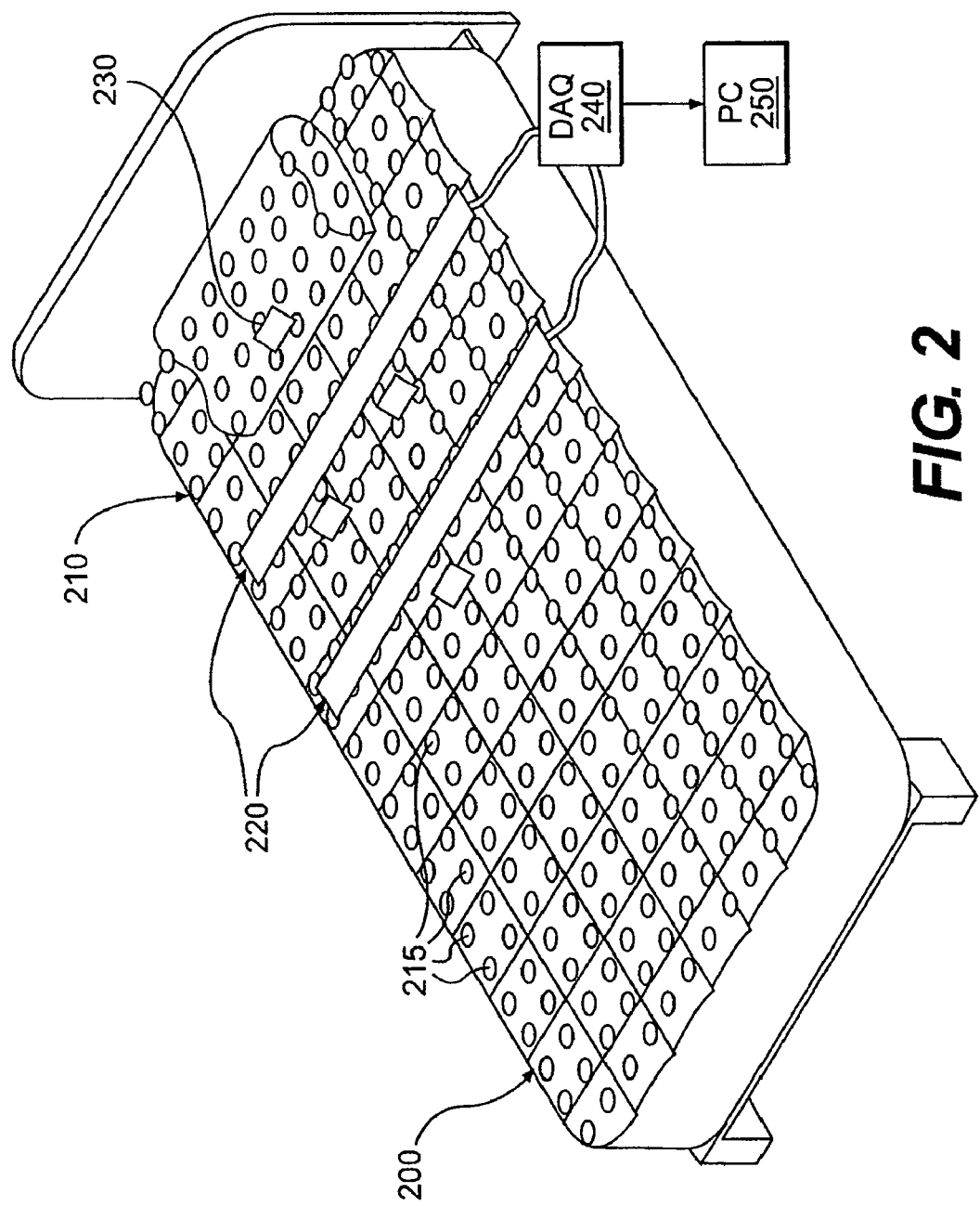
FIG. 2 illustrates an embodiment of a mattress pad layout containing a suite of sensors that may be employed in the system of the invention.

FIG. 2 illustrates an embodiment of a mattress pad layout containing a suite of sensors that may be employed in the invention to provide some or all of the input to data acquisition module 110. A mattress 200 may be any type of mattress or other support used by a person. An array 210 of pressure-sensitive switches 215 are arranged on the mattress 200 to determine the position of a subject when lying on the mattress 200. One suitable type of pressure switch is a pressure-activated binary, which is a transducer that provides an electrical signal upon a predetermined force or weight being applied to the sensor. While the term "switches" has been used, it is understood that various other types of sensors may also be used to determine the position of the subject, such as light sensors, and other sensors recognized by a skilled artisan. The switches 215 may be provided in a single apparatus, such as arranged in a mattress pad for placing over the mattress 200, or may be arranged individually on a mattress 200. A large number of switches 215 in a single apparatus thus may be placed over a mattress 200 in a relatively quick manner such that the switches 215 are arranged in the array 210 to obtain the desired degree of sensitivity.

Figure 3:
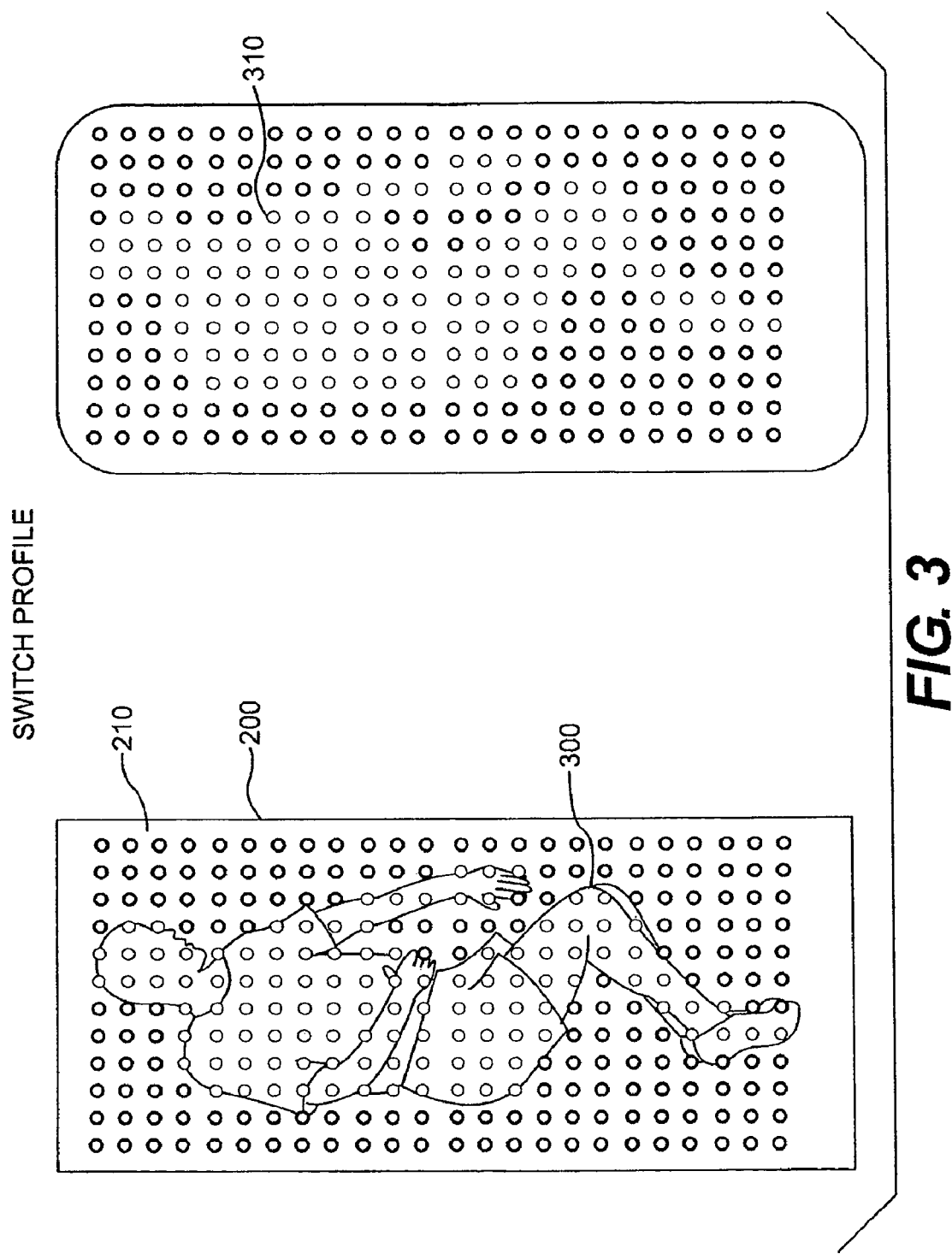
FIG. 3 illustrates a switch profile of the mattress pad layout described in FIG. 2.

FIG. 3 illustrates a switch profile that may be obtained from the mattress pad layout system of the invention, such as described in FIG. 2. As noted above, an array 210 of switches 215 is arranged on a mattress 200. A subject 300 is shown laying on the array 210. In this example, the switches activated by the subject (i.e., that are closed due to the weight of the subject) are shown as white, while those switches not activated (i.e. that are open) are shown as dark. The result is a switch profile 310 of the array 210, as shown without the subject 300. As shown, the activated switches 215 provide an approximate profile of the subject 300. As discussed above, output from the activated switches 215 is input into the system at mapping switch matrix 112 to be processed and/or analyzed to provide information about the position of the subject.

As described above, a matrix of momentary contact switches that are embedded in a mattress pad, block of foam or bed sheet may be used to provide a positional map of the person lying/sitting down. This positional map may be used in monitoring sleeping positions throughout the night, detecting the presence of a person in a bed or chair or detecting difficulty sleeping.

Figure 4:
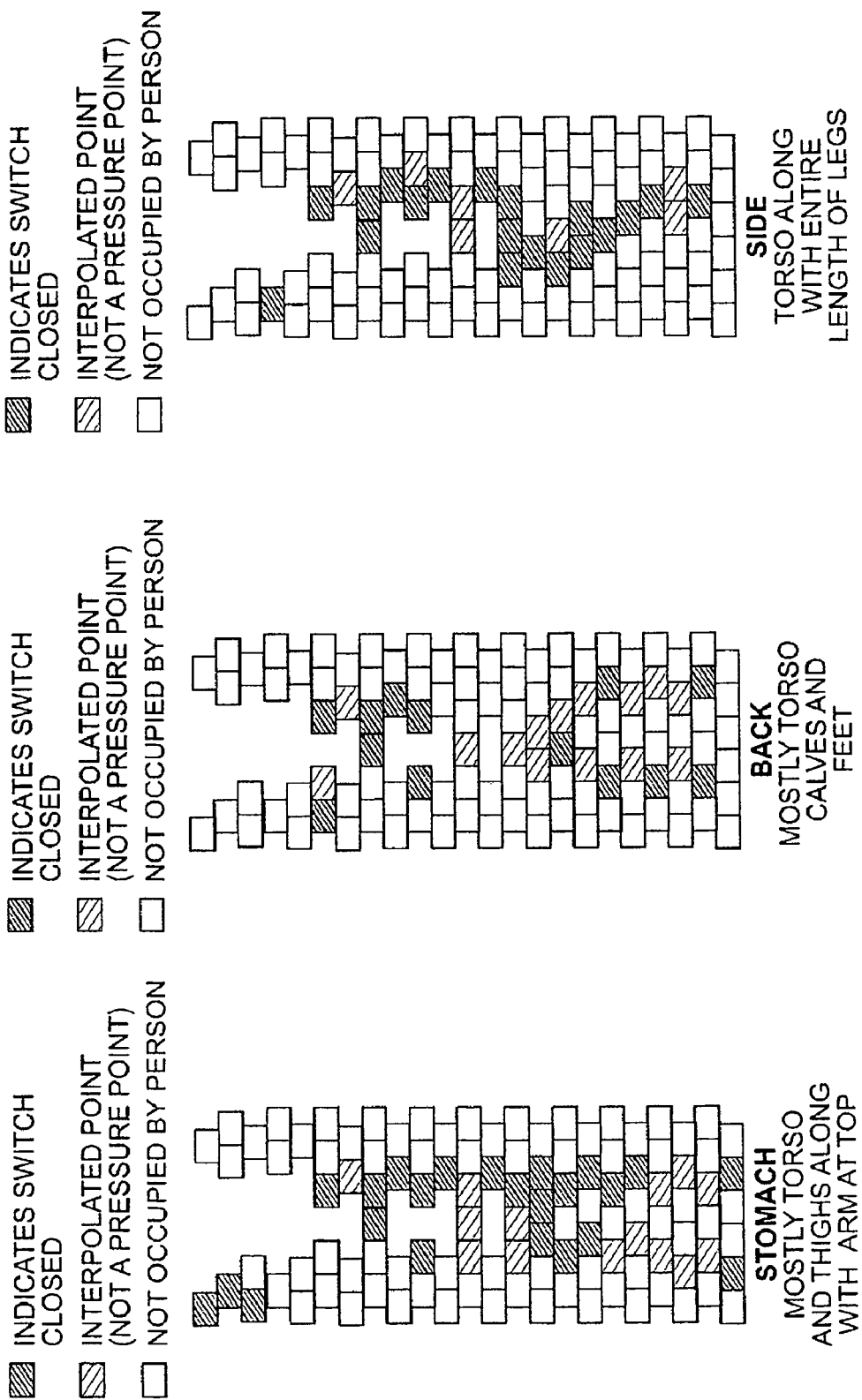
FIGS. 4A, 4B and 4C schematically illustrate graphical data indicative of the position of a subject, which may be produced from a mattress pad layout of the invention.

In particular, FIGS. 4A, 4B and 4C illustrate data that may be obtained from various switch profiles that may be produced from a mattress pad layout of the invention, which are called switch representations. The switch representations of FIGS. 4A, 4B and 4C are illustrated with white squares showing data from switches not occupied by the subject, gray squares showing data from switches indicating an interpolated point (i.e., some pressure but not sufficient to close the switch), and dark squares showing data from closed switches. FIG. 4A illustrates a switch representation where the subject was laying on his/her stomach. This results in activated switches to show mostly the torso and the thighs, along with an arm at the top of the array. FIG. 4B illustrates a switch representation where the subject was laying on his/her back. This results in activated switches to show mostly the torso, calves and feet. FIG. 4C illustrates a switch representation where the subject was laying on her side. This results in switches activated to show the torso along with almost the entire length of the legs.

Returning to the mattress pad layout of FIG. 2, one or more sensor pads 220 may extend transversely across the width of and are placed on the mattress 200. As described above, the sensor pads 220 may include ultra-sensitive vibration sensors, such as piezoelectric, fiber optic, or load cell based sensors that provide data, which may be input into the system at 120, and sensitive enough to provide through signal processing techniques, waveforms of heart rate, HRV, breathing rate, snoring and other physiological characteristics as described above. The vibration sensor pad 220 may be a foam pad with sensors embedded therein. Alternatively, the sensor pad 220 may be filled with air. The vibration sensor pads 220 may be placed at chest level (e.g., the rib cage) and abdomen level (e.g., below the rib cage), to provide readings of signals for heart rate and breathing. In addition, it may be desirable to have a vibration sensor pad 220 at leg level (e.g., calves) to read signals for heart rate.

The sensor pads 220 are connected to a data storage module 240. The sensors (e.g., switches 215, sensor pads 220, temperature sensors 230, etc.) and the data storage module 240 may form at least part of the data acquisition module 110 described above in FIG. 1. More specifically, data storage module 240 may include micro-controller 128. The connection may be via wires, or may use a wireless transmission. The data gathered by the data storage module 240 is then transmitted to a processor 250. Processor 250 may be a central processor, an Internet server, a personal computer (including a home personal computer), or any device that allows the processing of information. Further, the data may be stored in processor 250, or a module connected to processor 250, such as a storage device. Transmitting data may include a direct transfer, such as over a dedicated line, a closed network, the Internet, a wireless network, a WAN, or the like. Alternatively, transmitting the data may include storing the data on a readable medium and physically transferring the readable medium to the processor 250, where the processor accesses the data from the readable medium.

FIG. 2 also illustrates temperature sensors 230 which may be located on the mattress 200. In concert with the array of switches 210 and the vibrating sensor pads 220, the temperature sensors 230 obtain temperature data from the subject, which may be input into data acquisition module at 116 of FIG. 1.

In addition, temperature sensors may be embedded in a mattress pad, block of foam or bed sheet. The sensors may provide the surface body temperature of a subject that will be used to aid in the determination of sleep staging. This information may be used for controlling temperature, such as be activating the heat or the air conditioner. This information may also be used for activating white noise, soothing music, or electronically synthesized sound that would alter its sound profile based on the data obtained from the patient in order to provide a biofeedback signal to alter physiologic parameters in a way that might be deemed beneficial. Alternatively, the information may be used to drive a device that would touch the patient in various magnitudes and profiles.

Figure 5:
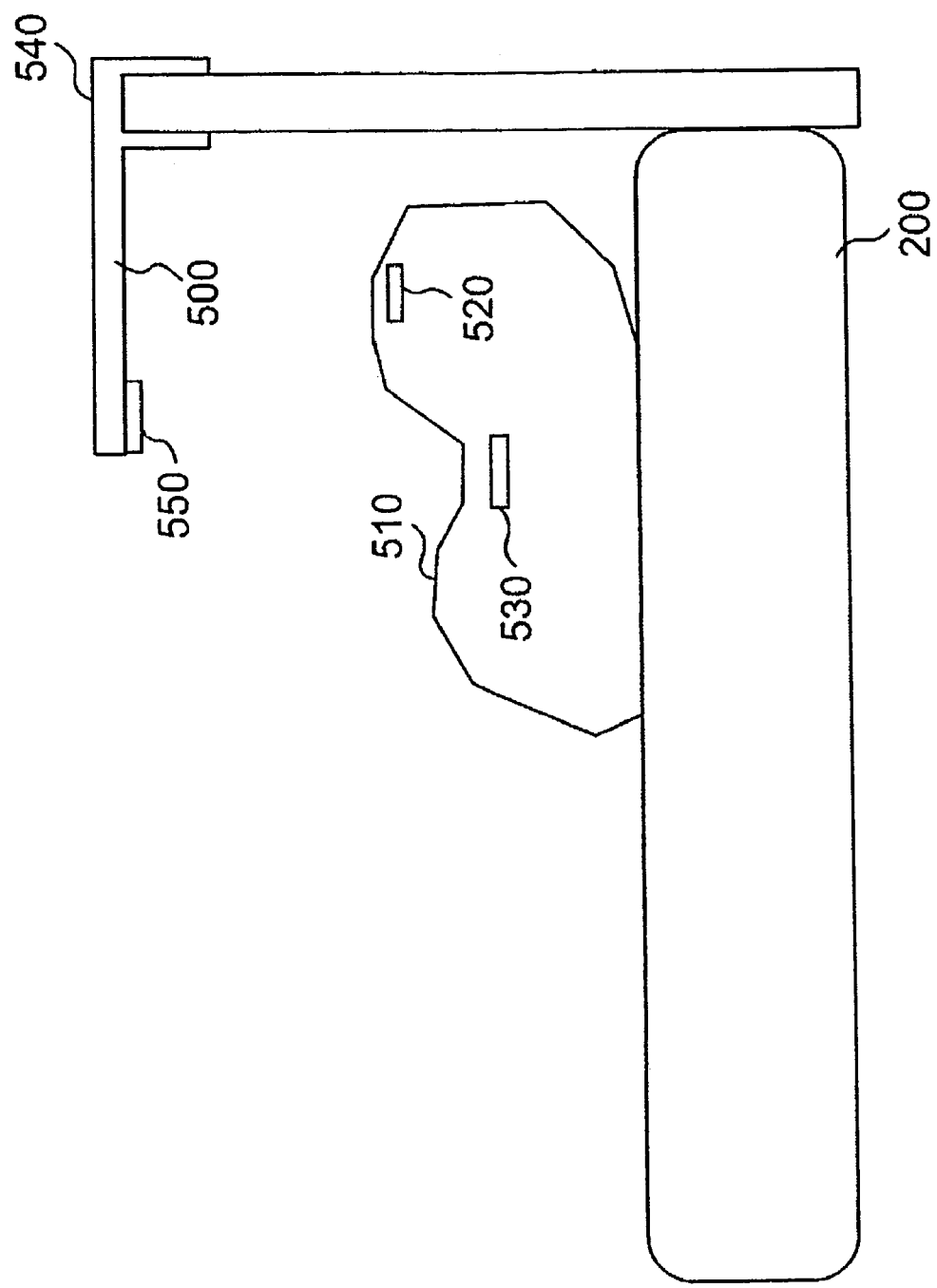
FIG. 5 illustrates an embodiment of a pillow layout system containing a suite of sensors that may be employed in the system of the invention.

FIG. 5 illustrates an embodiment of a pillow layout system containing a suite of sensors that may be employed in the invention. A pillow layout system 500 is located over the mattress 200. The pillow layout system includes a pillow 510, with at least one light sensor 520 and at least one humidity and/or carbon dioxide sensor 530. A swing arm 540 having at least one humidity and/or carbon dioxide sensor 550 may be fixedly or rotatably mounted to the support frame of the bed supporting mattress 200.

The light sensor 520 detects light to obtain data for analyzing ambient light conditions. Data from the light sensor is input at 124, as described above in FIG. 1. The humidity and/or carbon dioxide sensor 530 is used to obtain humidity data and carbon dioxide readings from the subject to obtain data for analyzing breathing rates, sleep patterns, and other respiratory information. Data from sensor 530 may be input into the micro-controller 128 of the data acquisition module 110, although that input is not specifically shown in FIG. 1.

Light sensors may quantitatively determine the light level in a room as part of a logic circuit that would determine if the person is actually sleeping on the bed or chair. In addition, humidity sensors may detect which direction a person's breathing is occurring in as an aid for positional analysis. By way of example, the humidity analysis information may be used in detecting of sleep apnea. In addition, carbon dioxide sensors may also be used in place of or in connection with the humidity sensors. Carbon dioxide sensors may determine absolute concentration of carbon dioxide in contact with the sensor, or may be a charge coupled device type sensor for imaging the carbon dioxide cloud that emerges from the subject upon exhalation for determining real time lung function.

Monitoring temperature and heart rate may be used to determine the sleep staging of a subject throughout the night as an assessment of the quality of sleep. The light level monitor may be used in a logic progression that determines if a person is actually asleep. Further, the information may be used to determine objective aspects of the Pittsburgh Sleep Index, as skilled artisans would recognize.

As the subject may switch positions on the pillow 510, thereby potentially covering one or more of the sensors, placing one or more sensors on the swing arm 540 above the pillow 510 allows data to be obtained. Further, the swing arm 540 may move, based on the movement of the subject, to allow data to be obtained. According to one feature, one or more pressure switches (not shown) in the pillow 510 may be connected to the swing arm 540. The swing arm may include a motor to extend, retract, or rotate the arm based on the subject's position.

The light sensor 520 and the humidity and/or carbon dioxide sensor 530 may be incorporated within a covering for the pillow 510. Alternatively, the light sensor 520 and the humidity and/or carbon dioxide sensor 530 may be incorporated directly into the pillow 510. The swing arm 540 may be attached to a headboard of the bed. Alternatively, the swing arm 340 may be attached directly to a wall or to a post forming part of the bed that allows the sensors to be located above the head of a subject.

Figure 6:
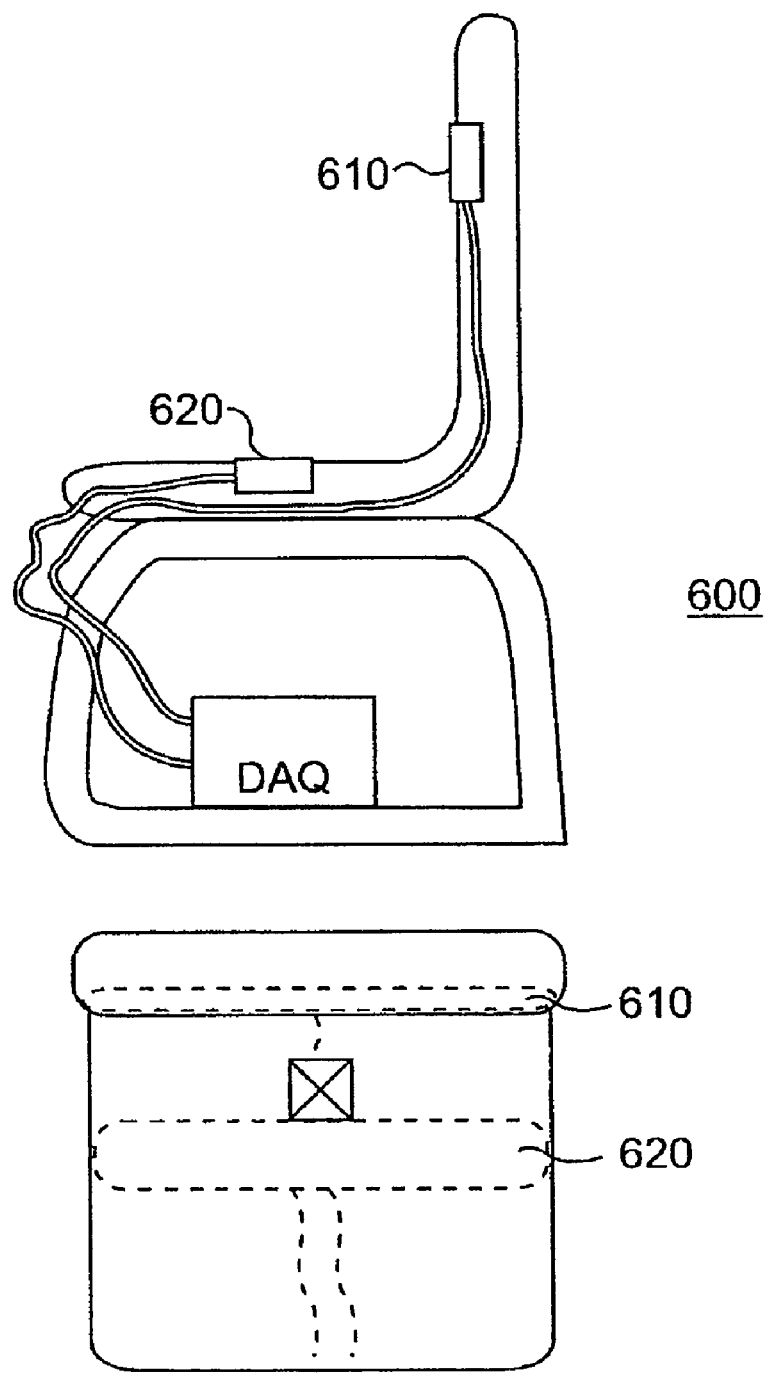
FIG. 6 illustrates an embodiment of a chair layout containing a suite of sensors that may be employed in the system of the invention.

FIG. 6 illustrates an embodiment of a chair layout containing a suite of sensors that may be employed in a system constructed according to the principles of the invention. A chair 600 has a vibration sensor pad 610 placed in the back of the chair, another vibration sensor pad (not shown) in the seat of the chair and a temperature sensor 620 placed in the seat of the chair 600. The vibration sensor pad 610 may be identical to vibration sensor pad 220 described above, but adapted to a chair. Further, a data storage module 630 may be placed under the chair. Data storage module 630, along with vibration sensor pad 610 and temperature sensor 620 may be included in data acquisition module 110 of FIG. 1. Data storage module 630 may correspond to micro-controller 128. Although not shown, a swing arm or other proximal sensor with one or more sensors also may be placed above the chair. While only two sensors 610 and one temperature sensor 620 are shown, it is understood that a plurality of sensors 610 and temperature sensors 620 may be used. The invention may be incorporated into other devices besides beds and chairs, such as wheelchairs, couches or other objects for sitting or lying.

As described below, electronic components and circuits may be used to reduce noise and increase gain of the vibration sensor's transducer. The design, use and combination of filters isolate specific frequencies so as to divide the signals from the heart rate and respiration. For example, when used in conjunction with appropriate sampling rates, respiration and heart rate waveforms may be obtained. In addition, heart rate variability may be determined and sleep apnea may be detected.

Figure 7:
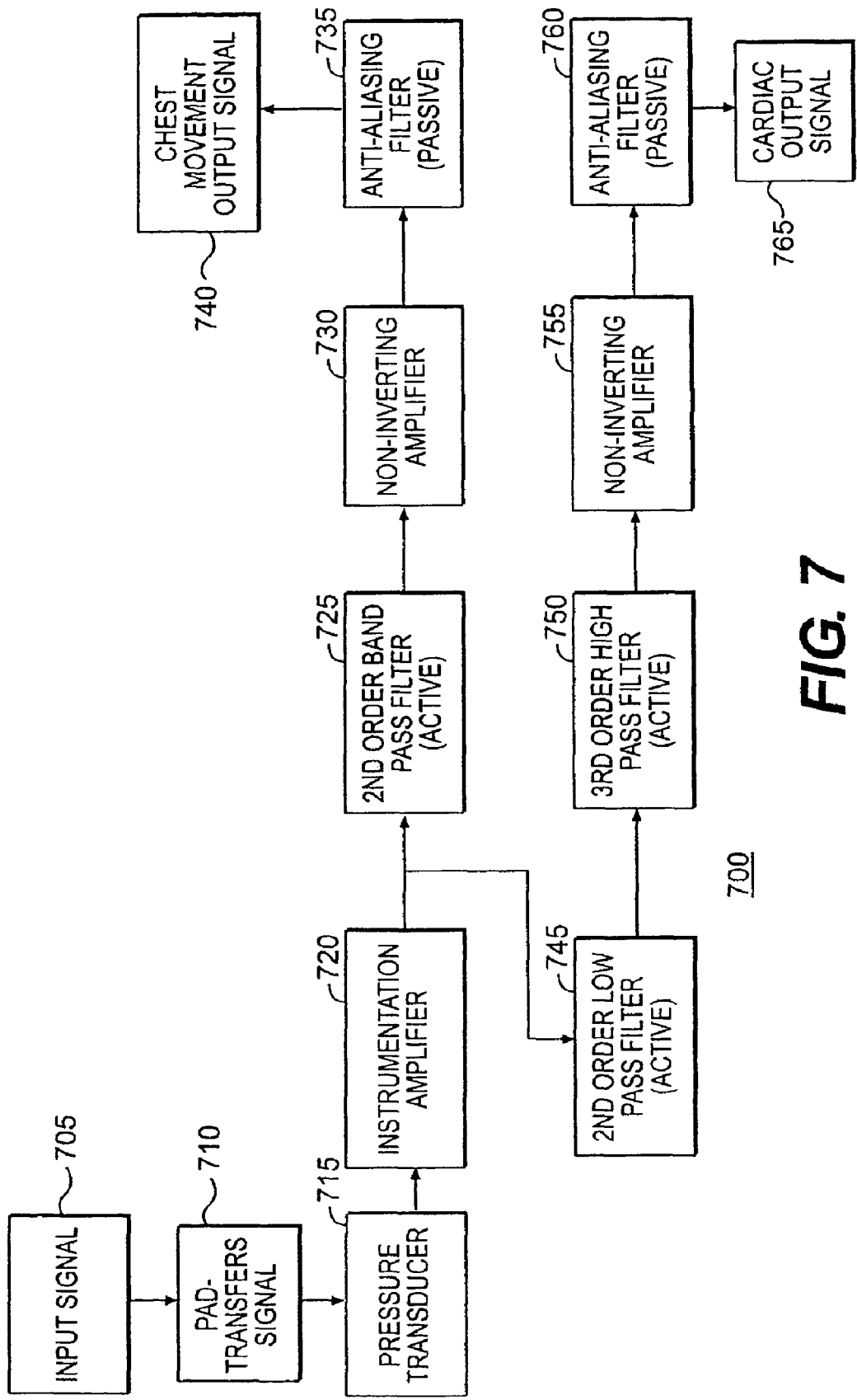
FIG. 7 is a block diagram illustrating a first embodiment of a system of the invention for separating respiratory and cardiac output signals obtained from pressure transducers sensing chest and abdomen movement.

FIG. 7 is a block diagram illustrating a first embodiment of a system for separating respiratory and cardiac output signals of vibration sensors constructed according to the principles of the invention. The system 700 receives an input signal 705 from the subject by way of signals transferred from the sensor pads 710 and through a pressure transducer 715. The signal is received at an instrumentation amplifier 720, which may provide adequate buffering when, for example, a piezoelectric sensor is used and an infinite common mode rejection ratio (CMRR) is used to reduce sensitivity to noise. At the output of the instrumentation amplifier the signal may be split. A first output of the instrumentation amplifier is provided to a first filter 725, which may be a second order band pass filter with both cutoff frequencies below about 1 Hz and may be an active filter. The output of the first filter 725 is amplified by a non-inverting amplifier 730, and then filtered through a second filter 735. The second filter 735 may be an antialiasing filter and a passive filter. The second filter 735 outputs a chest movement output signal 740. From the chest movement output signal 740, the breathing rate of a subject may be obtained.

The second output of amplifier 720 is provided to third filter 745, which may be a second order low pass filter with a cutoff frequency below about 1 Hz and an active filter. The output of the third filter 745 is provided to a fourth filter 750, which may be a third order high pass filter with the cutoff frequency below about 50 Hz and an active filter. The output of the fourth filter 750 amplified by a non-inverting amplifier 755, and then filtered through a fifth filter 760. The fifth filter 760 may be an antialiasing filter and a passive filter. The fifth filter 760 outputs a cardiac output signal 765. From the cardiac output signal 765, the heart rate of a subject may be obtained. By way of example, components 720-735 and 745-760 may be implemented through digital signal processing.

Figure 8:
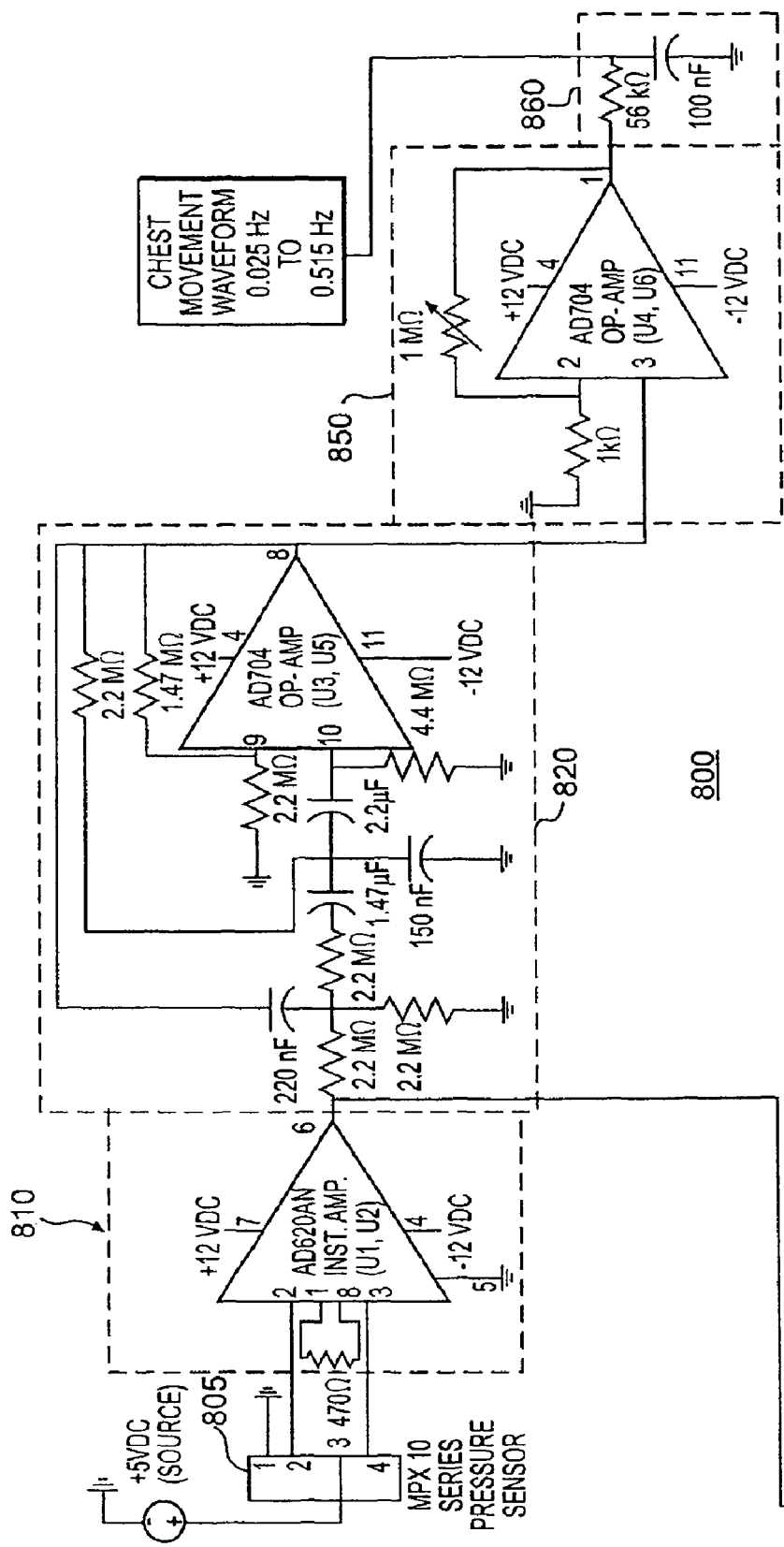
FIG. 8 illustrates a first embodiment of the amplifier and filter circuit constructed according to the principles of the invention that may be used to process physiological signals obtained from a vibration sensor.
Figure 8:
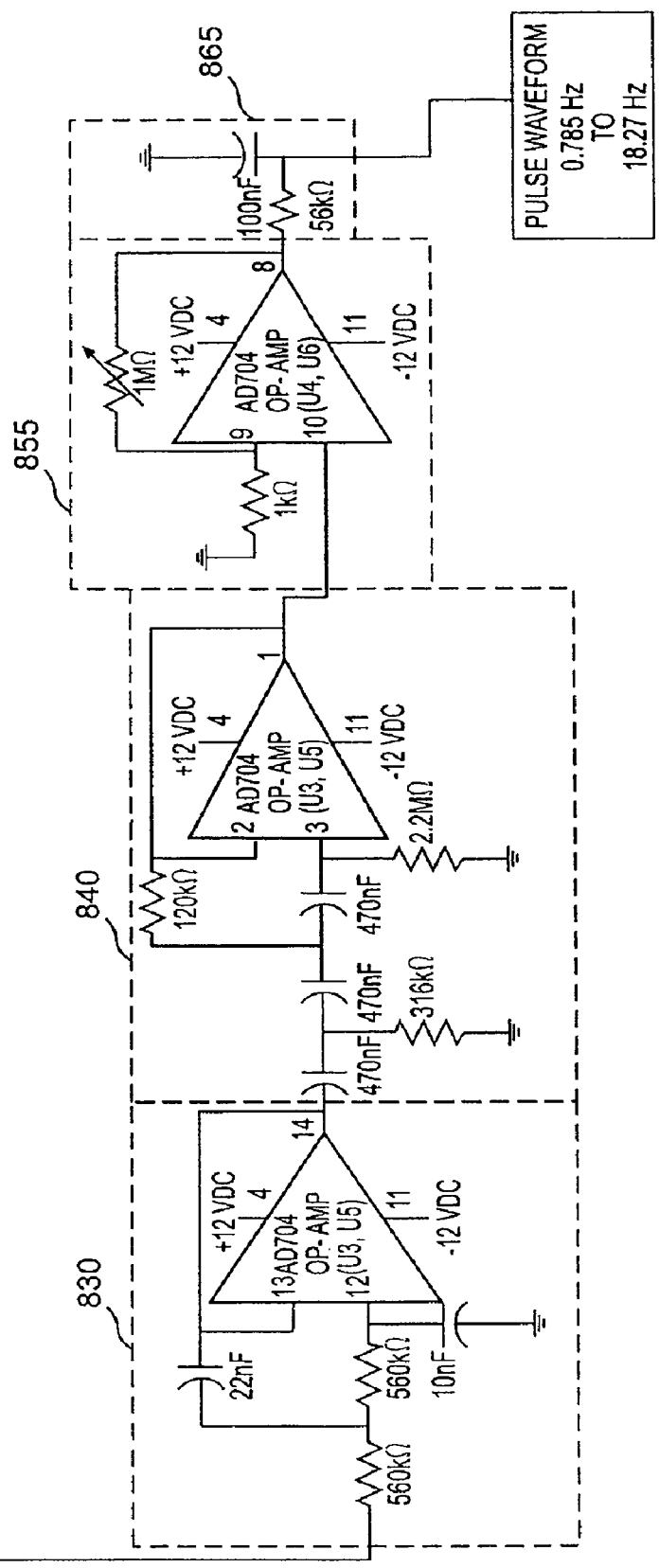

FIG. 8 illustrates a first embodiment of the amplifier and filter circuit constructed according to principles of the invention that may be used to process physiological signals obtained from a vibration sensor. A sensor 805 is connected to an instrumentation amplifier 810. The sensor 805 maybe, for example, a pressure sensor in a sensor pad 220 used in a mattress layout as shown in FIG. 2, and whose output is input at 120 in data acquisition module 110 described in FIG. 1. The output signal from the instrumentation amplifier 810 is fed into a second order band pass filter 820 and into a second order low pass filter 830. The output signal from the second order band pass filter 820 is fed into a first non-inverting amplifier 850. The output signal from the first non-inverting amplifier 850 is fed into a first low pass, passive filter 860. The output signal from the first low pass passive filter 860 results in a waveform corresponding to the chest movement of the subject. By way of example, the waveform corresponding to the chest movement may be in a range of between about 0.025 and about 0.515 Hz.

As described above, the output signal from the instrumentation amplifier 810 is also fed into a second order low pass filter 830. The output signal from the second order low pass filter 830 is fed into a third order high pass filter 840. The output signal from the third order high pass filter 840 is fed into a second non-inverting amplifier 855. The output signal from the second inverting amplifier 855 is fed into a second low pass passive filter 865. The output signal from the second low pass passive filter 865 results in a waveform corresponding to the pulse of the subject. By way of example, the waveform corresponding to the pulse may be in a range of between about 0.785 and about 18.27 Hz.

Figure 9:
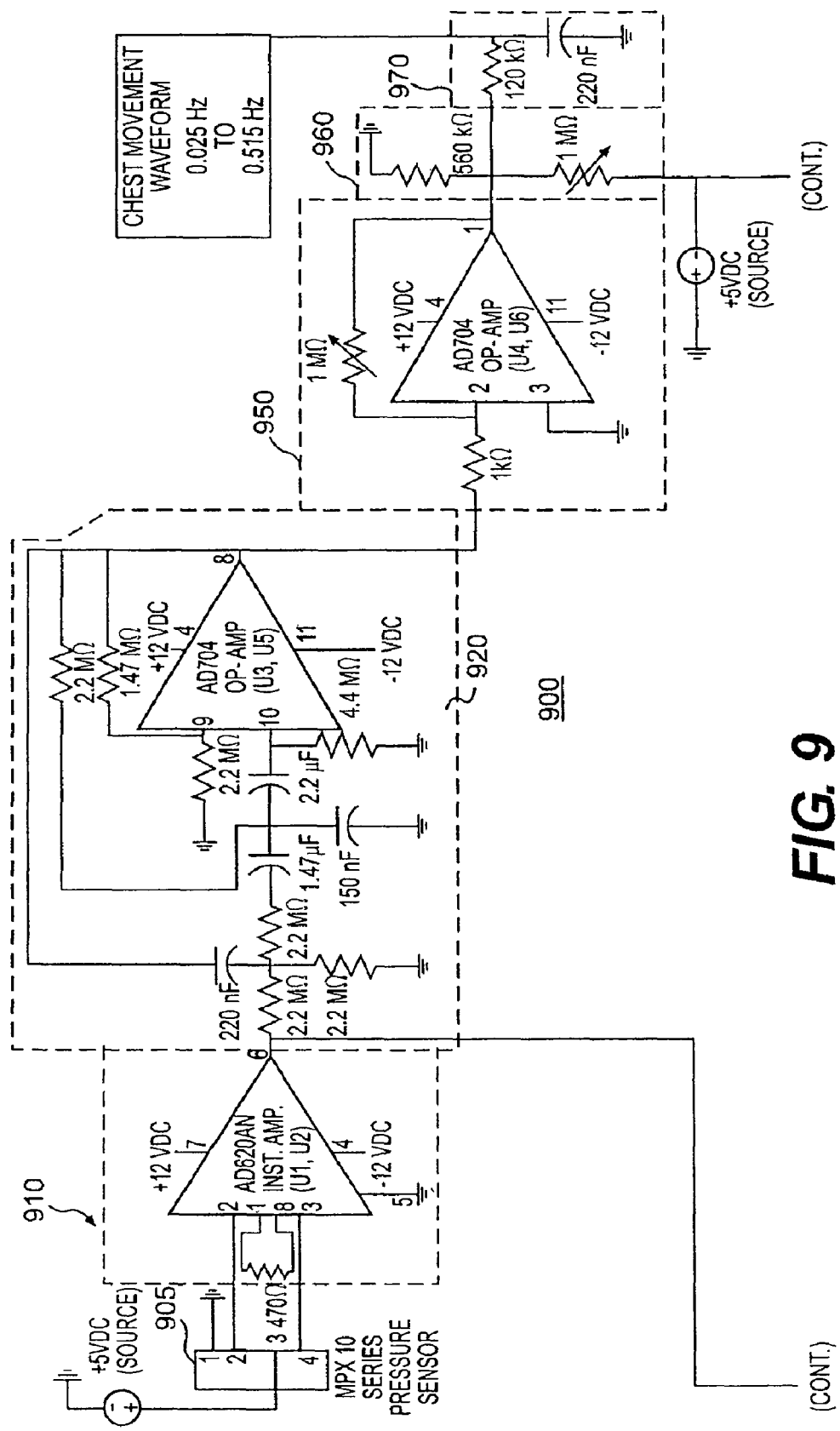
FIG. 9 illustrates a second embodiment of an amplifier and filter circuit constructed according to the principles of the invention that may be used to process physiological signals obtained from a vibration sensor.
Figure 9:
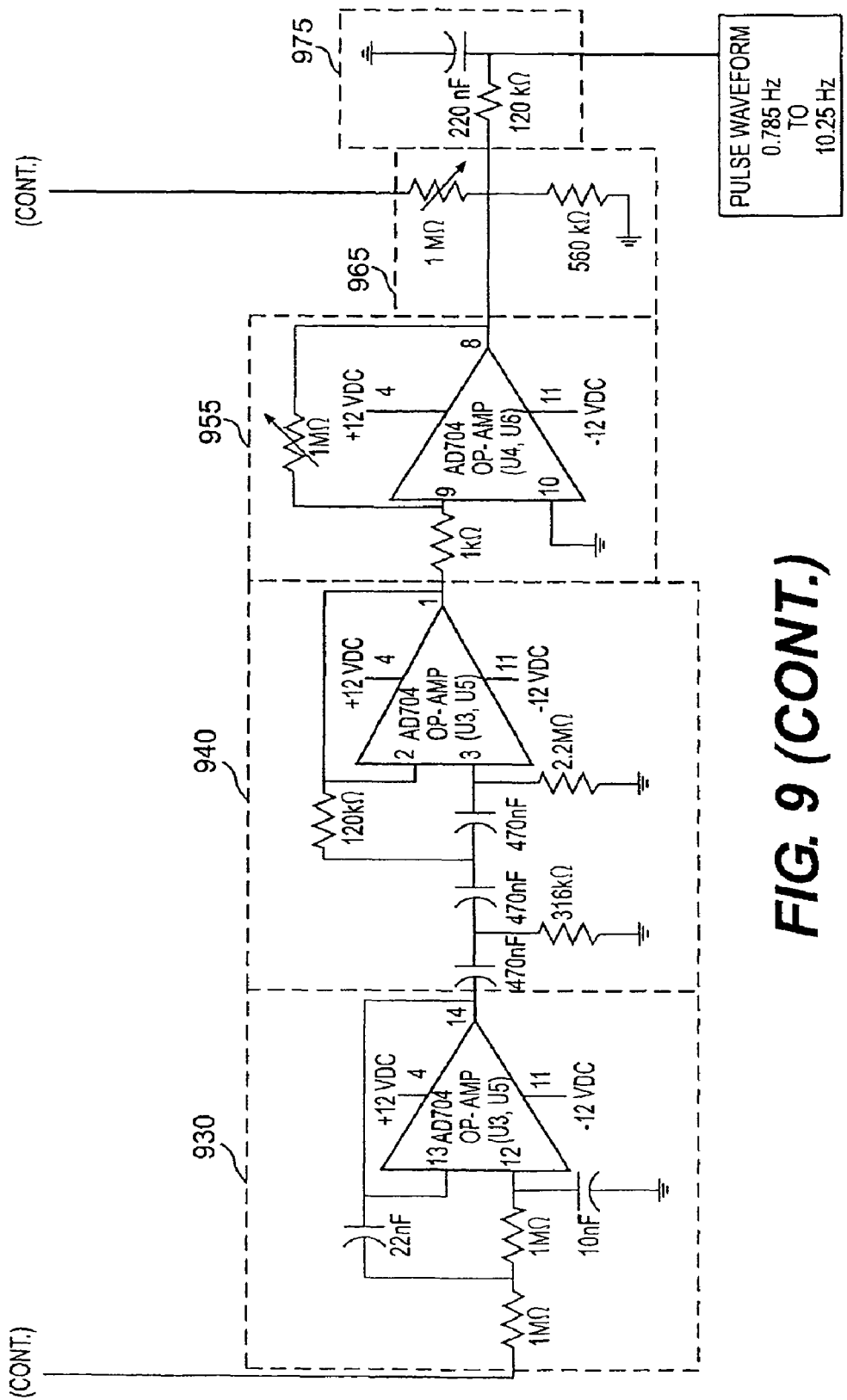

FIG. 9 illustrates a second embodiment of an amplifier and filter circuit constructed according to principles of the invention that may be used to process physiological signals obtained from a vibration sensor. A sensor 905 is connected to an instrumentation amplifier 910. The sensor 905 may be, for example, a pressure sensor. The output signal from the instrumentation amplifier 910 is fed into a second order band pass filter 920 and into a second order low pass filter 930. The output signal from the second order band pass filter 920 is fed into a first inverting amplifier 950. The output signal from the first inverting amplifier 950 has a bias voltage 960 applied, and-the resulting signal is fed into a first low pass passive filter 970. The output signal from the first low pass passive filter-970 results in a waveform corresponding to the chest movement of the subject. By way of example, the waveform corresponding to the chest movement may be in a range of between about 0.025 and about 0.515 Hz.

As described above, the output signal from the instrumentation amplifier 910 is also fed into a second order low pass filter 930. The output signal from the second order low pass filter 930 is fed into a third order high pass filter 940. The output signal from the third order high pass filter 940 is fed into a second inverting amplifier 955. The output signal from the second inverting amplifier 955 has a bias voltage 965 applied, and the resulting signal is fed into a second low pass passive filter 975. The output signal from the second low pass passive filter 975 results in a waveform corresponding to the pulse of the subject. By way of example, the waveform corresponding to the pulse may be in a range of between about 0.785 and about 10.25 Hz.

The circuit 900 has a lower cutoff frequency than the circuit 800 of FIG. 8. This may reduce or eliminate aliasing due to the lower sampling rate of the micro-controller, such as the micro-controller described below. Further, the biasing voltages 970 and 975 may add a DC offset to center the signal in an analog-to-digital converter's active range detection.

As described above, the microcontroller/microprocessor module may acquire the data from all of the sensors and turn it into a bit stream pattern. The bit stream pattern may then be logged by a processor into a data file for immediate analysis or for later review. By way of example, the bit stream may be produced by the momentary contact switches and fed into the microcontroller/microprocessor through the use of shift-registers to provide a positional map of the person on the mattress pad, block of foam, bed sheet, or other support. This map may be used in conjunction with the humidity and carbon dioxide sensors to determine the exact position of the individual or to detect movements.

Figure 10:
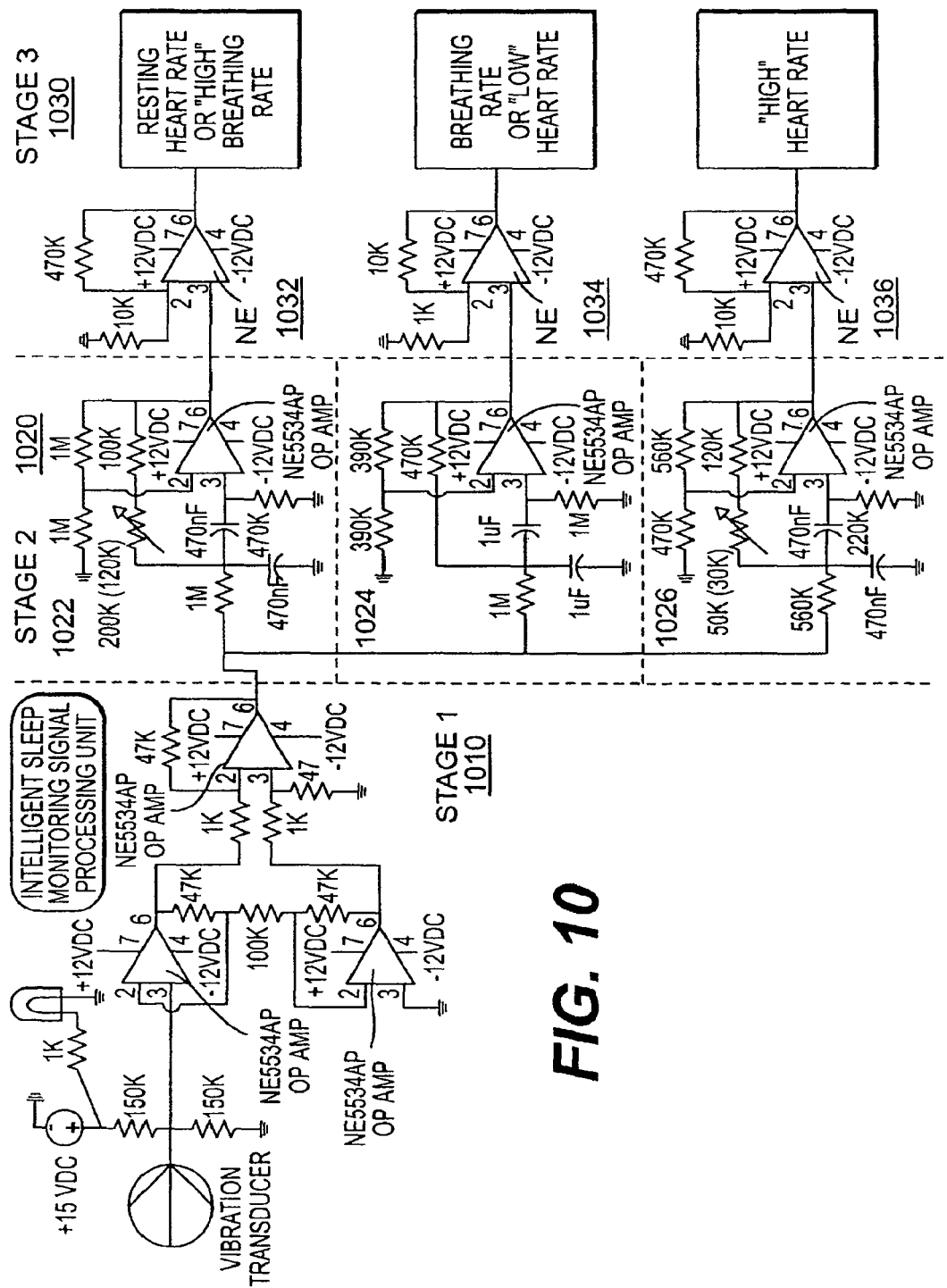
FIG. 10 illustrates a third embodiment of an amplifier and filter circuit constructed according to the principles of the invention that may be used to process physiological signals obtained from a vibration sensor.

FIG. 10 illustrates a third embodiment of an amplifier and filter circuit constructed according to principles of the invention that may be used to process physiological signals obtained from a vibration sensor. The circuit 1000 may be used within a process and system of the invention to process physiological signals obtained from a sensor of the invention such as a vibration sensor shown at 120. An ultra-sensitive vibration (such as a piezoelectric, fiber optic or load cell based) sensor may be used that, through the signal processing techniques in the circuit 1000, can provide waveforms indicative of both heart rate and breathing rate. Circuit 1000 may be provided in an analysis routine, such as in analysis 156.

In the example of circuit 1000, the raw signal from the vibration transducer sensor 1005 (which can be replaced with other types of sensors) is sent through a series of amplifiers and filters to separate the signal into useable waveforms. At the first stage 1010, which amplifies the signal, the signal is initially passed through a 3-op-amp amplifier, which has an infinite common mode rejection ratio (CMRR). Other types of amplifiers known in the art may also be used.

At the second stage 1020, the signal is then passed through three different filters. The filters in the second stage 1020 include a first filter 1022, a second filter 1024 and a third filter 1026. The first filter 1022 may be a bandpass filter from about 0.1 to about 0.8 Hz. The second filter 1024 may be a bandpass filter from about 0.8 to about 1.5 Hz. The third filter 1026 may be a bandpass filter from about 1.5 Hz to about 3 Hz. Thus, the signal is separated into three different channels in the second stage 1020. At the third stage 1030, which amplifies the signals, the signals are then passed through respective non-inverting amplifiers 1032, 1034 and 1036 that increase the dynamic range and signal to noise ratio of the signal. These three outputs are then sent through an analog-to-digital converter (not shown) before being sent to a micro-controller module as described below in reference to FIG. 9. This micro-controller corresponds to micro-controller 128 described in FIG. 1 above. An example of such a micro-controller is the BASIC Stamp 2 module commercially available from Parallax, Inc.

Figure 11:
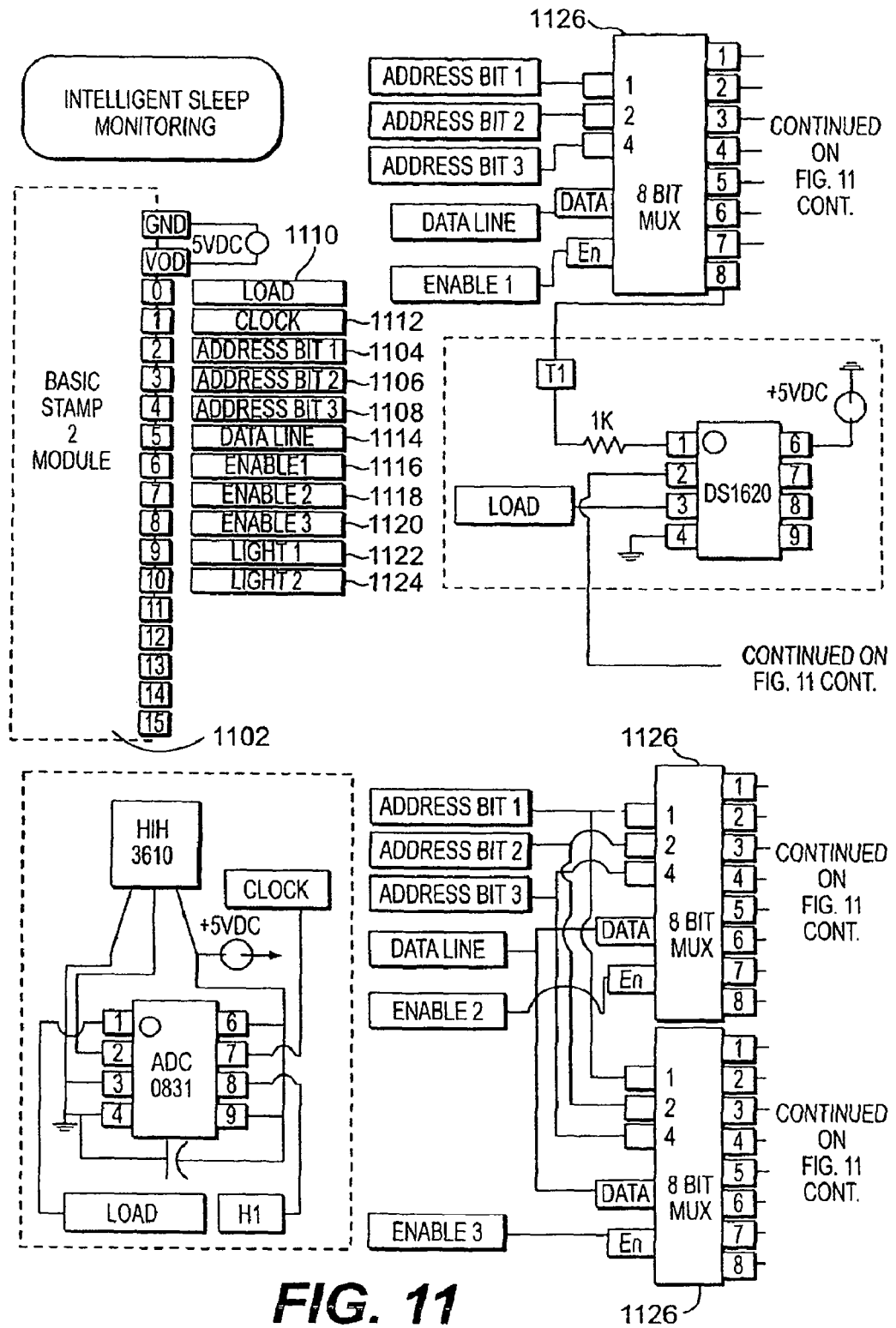
FIG. 11 illustrates a micro-controller module circuit constructed according to the principles of the invention that may be used to process electronic signals from an amplifier and filter circuit of the invention.
Figure 11:
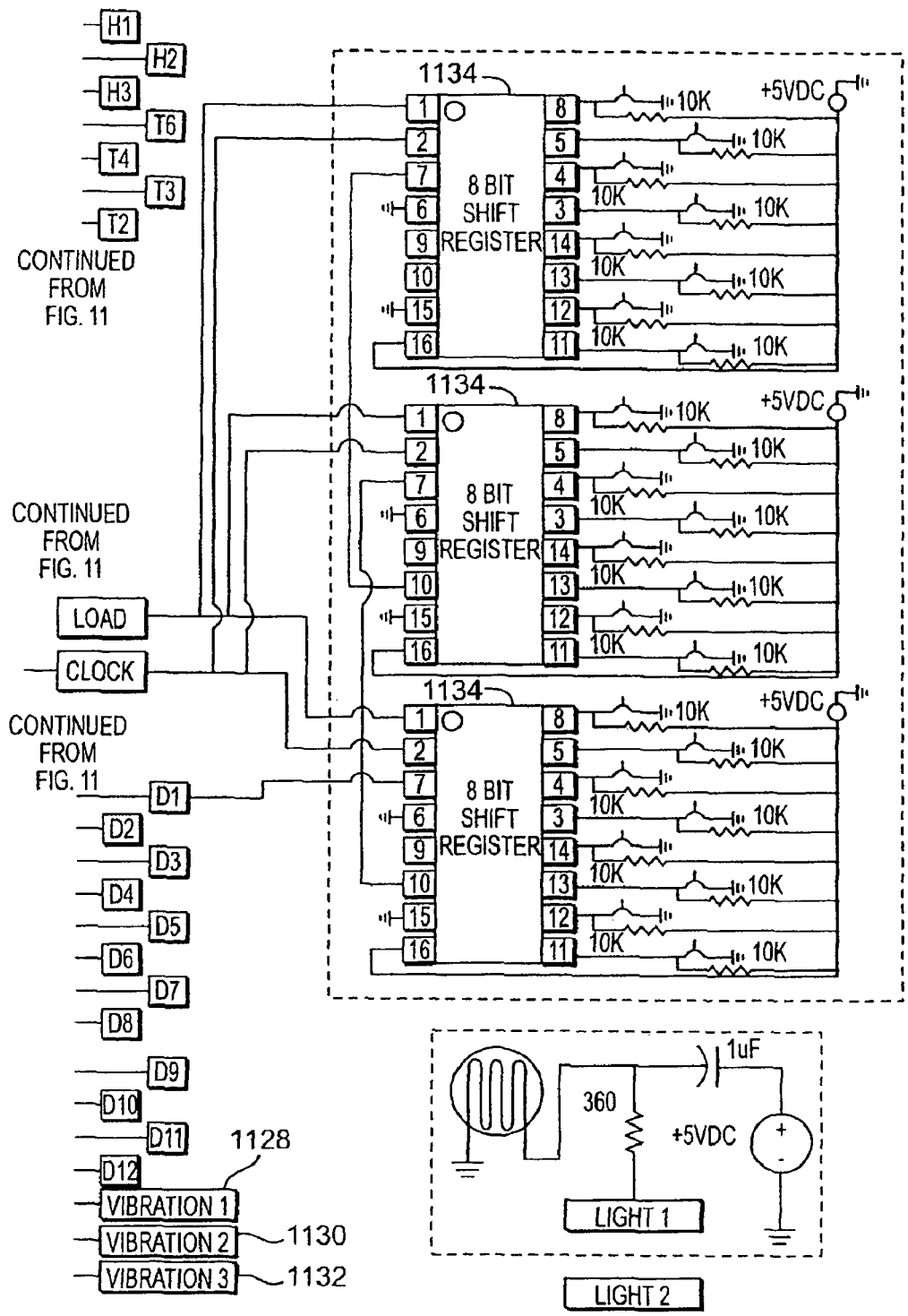

Thus, temperature sensors, carbon dioxide sensors, light sensors, humidity sensors, electromagnetic sensors, and simple momentary contact switches form a passive sensor suite that provides multi-dimensional data about the user without the use of any type of camera or microphone equipment. FIG. 11 illustrates a micro-controller for receiving the signals from a circuit, such as circuit 1000 illustrated in FIG. 10. A micro-controller module 1102 is shown having three address lines 1104, 1106, and 1108. In addition, the micro-controller module 1102 has a load line 1110, a clock line 1112, a data line 1114, enable lines 1116, 1118 and 1120, and light lines 1122 and 1124.

To accommodate the large amount of switches being employed in the circuit 1100, several 8-bit parallel load serial shift registers 1134 are employed to shift in all of the switches into just three pins on the micro-controller module 1102. Address lines 1104, 1106 and 1108 are used to address the chips 1126 connected in parallel to the micro-controller 1102. The enable lines 1116, 1118 and 1120 select the chip 1126 and the address lines 1104, 1106 and 1108 select the input for the selected chip. The outputs of FIGS. 8, 9 or 10 are provided in vibration lines 1128, 1130 and 1132.

Figure 14:
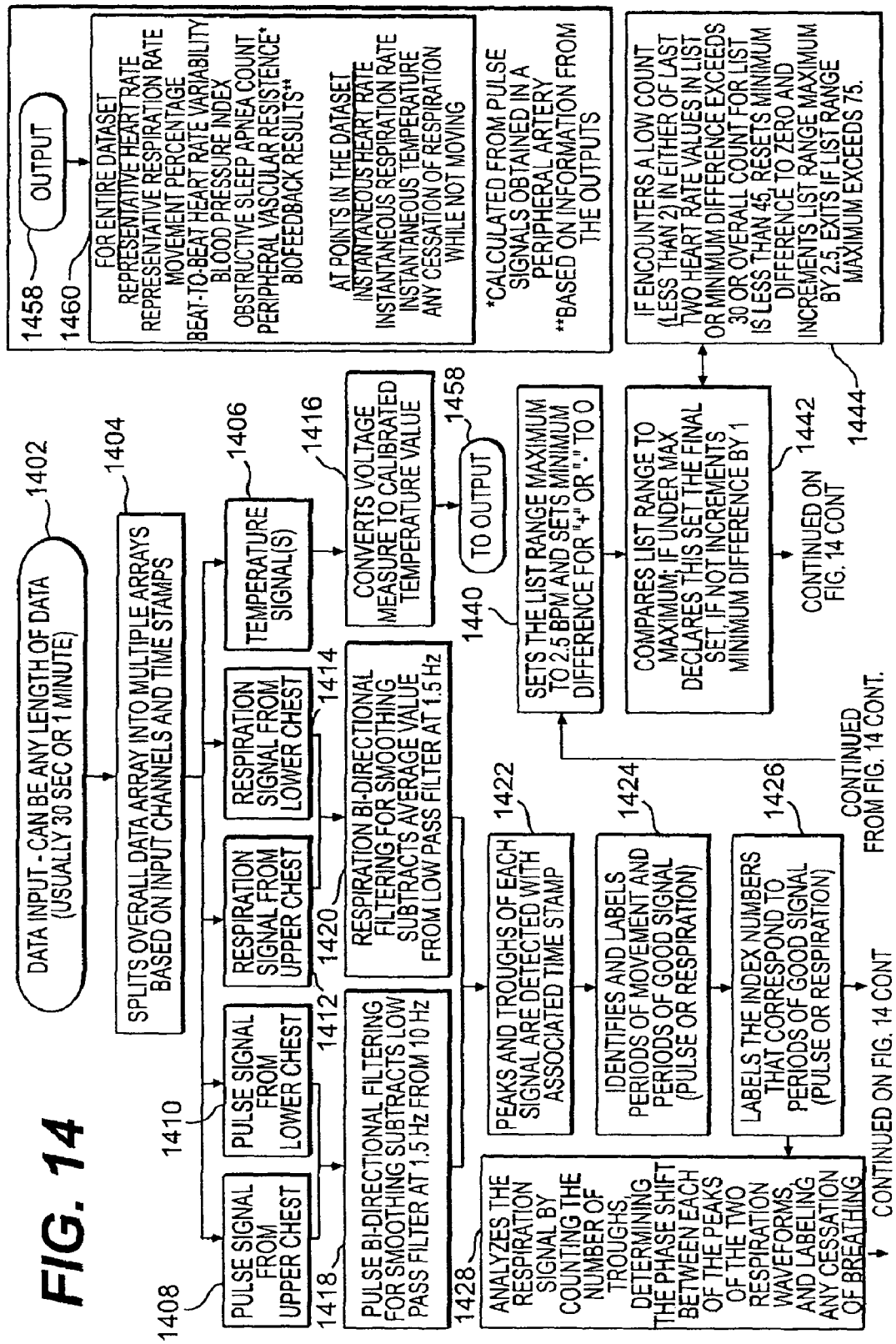
FIG. 14 is a block diagram of an algorithm for analyzing the processed signals according to principles of the invention.
Figure 14:
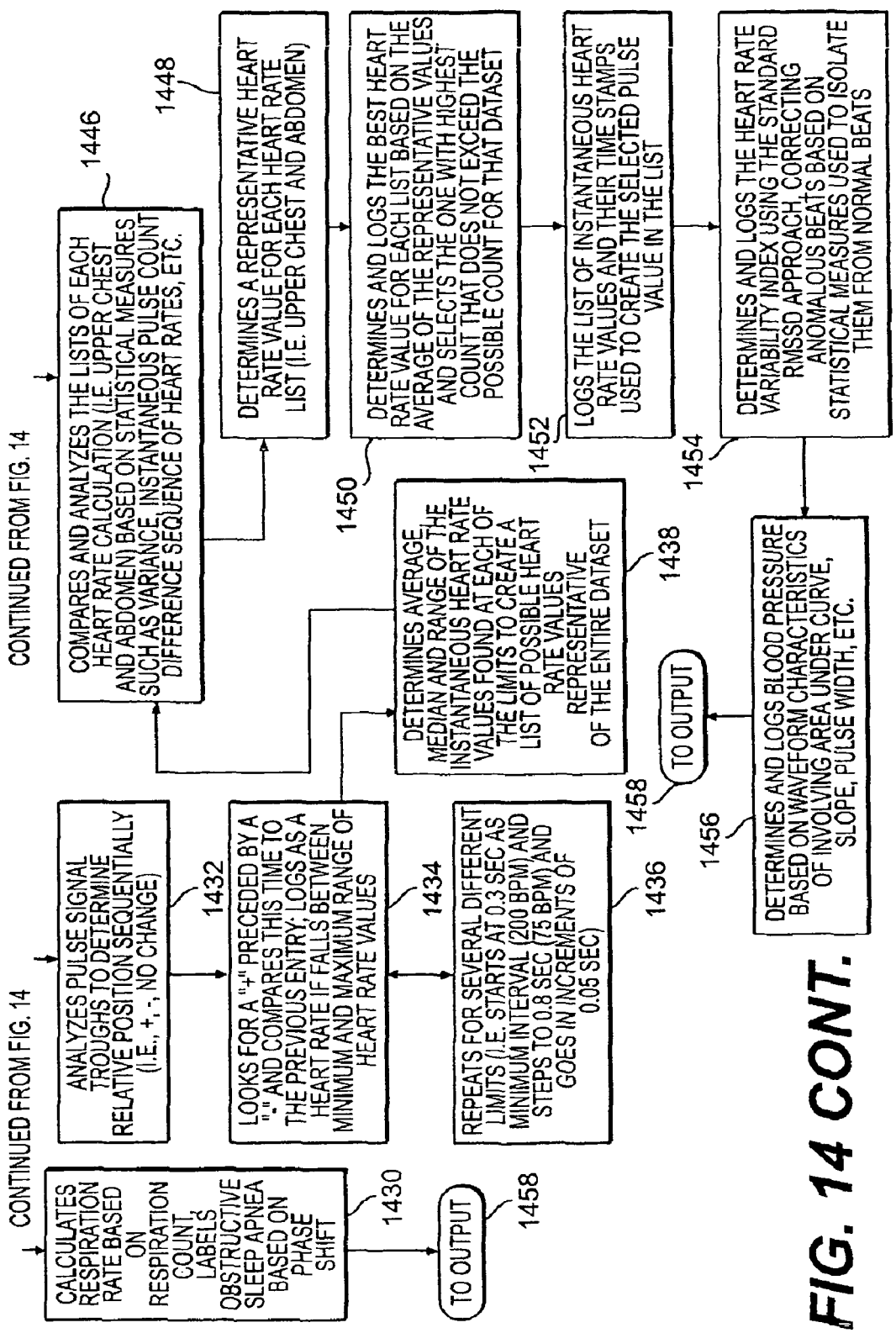

FIG. 14 is a block diagram of an algorithm for analyzing the processed signals according to principles of the invention, such as shown in the flow chart of FIG. 1 at 164. Data is input at 1402. The data may be data that has been gathered for any length of time. For example, the data may have been gathered for 30 seconds or one minute. The data is then split into multiple arrays at 1404. The multiple arrays are based on the input channels (e.g., which sensor the data came from) and the time stamp associated with the data. As shown, the data is divided into temperature signal(s) 1406, pulse signals from the upper chest 1408, pulse signals from the lower chest 1410, respiration signal from upper chest 1412, and respiration signal from lower chest 1414.

The voltage measured in the temperature signal(s) 1406 is converted to the calibrated temperature value 1416. The temperature value is then sent to output 1458.

The pulse signals from the upper chest 1408 and the pulse signals from the lower chest 1410 have recursive bi-directional filtering performed at 1418. This filtering may smooth the waveform and subtract data smoothed with a low pass frequency of about 1.5 Hz from data smoothed at a low pass frequency of about 10 Hz. The respiration signal from upper chest 1412 and the respiration signal from lower chest 1414 have recursive bi-directional filtering performed on them at 1420 to create a combined respiratory signal. This filtering may smooth the waveform and subtract average values of the dataset from data smoothed with 1.5 Hz filters.

The peaks and troughs of the filtered signals are detected with the associated time stamp at 1422. The periods of movement by the subject and the periods of good signal for the pulse and the respiration are identified and labeled at 1424. The index numbers that correspond to the periods of good signal are labeled at 1426. The index numbers indicate the sample numbers that contain usable signal data as opposed to movement artifact.

The respiration signal is analyzed by counting the number of troughs at 1428. The respiration rate is further analyzed by determining the phase shift between each of the peaks of the two respiratory waveforms and labeling any cessation in breathing. The respiration rate is calculated based on the respiration count at 1430. Sleep apneas may be labeled based on the phase shift. This information in then sent to output 1458.

Pulse signal troughs are analyzed to determine the relative position, sequentially, at 1432. The relative position is indicated as a "+," a "−" or no change. If a trough is positioned above a previous one, it receives a "+." If the opposite occurs, the trough gets a . . . The signal troughs are examined to find any instances of a trough marked with a "+" that is preceeded, i.e., before by a trough marked with a "−." The time stamp associated with this trough is compared to the previous entry and the difference is logged as a heart rate if it falls between the minimum and maximum range of heart rate values. This is repeated several times at 1436 with several different limits. For example, 0.3 seconds is marked as the minimum interval (200 beats per minute), and steps up by increments of 0.05 seconds (e.g., 0.35 seconds, 0.40 seconds, etc.). This produces a list of possible heart rates given the imposed limits or the algorithm's maximum allowable heart rate, thereby reducing the chance for larger errors.

At 1438, the average, median and range of the instantaneous heart rate values is determined for each of the limits to create a list of possible heart rate values representative of the entire data set. The maximum list range is set to 2.5 beats per minute at 1440. Further, the minimum difference for the "+" and "−" is set at zero. The list range is compared to the maximum at 1442. If the list range is under the maximum, the set is declared the final set. If the list range is not under the maximum, the minimum difference is incremented by one. Thus, small troughs are increasingly discarded as noise so as to isolate the true heart rate signals. If a low count is encountered (e.g., less than two) in either of the last two heart rate values in the list, if the minimum difference exceeds 30, or if the overall count for the list is less than forty-five, the minimum difference is reset to zero. Further, this increments the list range maximum by 2.5 and then repeats the process. The algorithm exits this step if the list range maximum exceeds 75.

The lists of each heart rate calculation (i.e., upper chest and abdomen) are compared and analyzed at 1446 based on statistical measures. The statistical measures include, but are not limited to, variance, instantaneous pulse count difference, and sequential difference of heart rates. A representative heart rate value for each heart rate list (i.e., upper chest and abdomen) is determined at 1448.

The best heart rate value for each list is determined and logged at 1450. Determining the best heart rate value may be based on the average of the representative values and selecting the one value with the highest count that does not exceed the possible count for the data set. The list of instantaneous heart rate values and their time stamps used to create the selected pulse value in the list are logged at 1452.

The heart rate variability index is determined and logged at 1554 using the standard root mean square of sequential differences (RMSSD) approach. Anomalous beats are corrected based on statistical measures used to isolate the anomalous beats from normal beats. Blood pressure is determined at 1456 based on, but not limited to, the waveform characteristics involving the area under the curve, the slope of the curve, and the pulse width. This information is also logged. This information in then sent to output 1458.

Output 1458 for the entire data set 1460 may comprise numerous types of information. By way of example only, the information may include a representative heart rate, a representative respiratory rate, movement percentage, beat-to-beat heart rate variability, blood pressure index, obstructive sleep apnea count, peripheral vascular resistance, and biofeedback results. Other information may include an instantaneous heart rate, an instantaneous respiration rate, an instantaneous temperature, and any cessation of respiration while not moving.

Using the apparatus and processes described above, numerous embodiments may be constructed and used to measure physiological characteristics of a subject. Examples of these embodiments and the features that may be achieved by these embodiments are described below. Features of one embodiment may be employed in other embodiments, even if not explicitly stated herein. According to an embodiment of the invention, the temperature sensors, carbon dioxide sensors, light sensors, electromagnetic sensors and the array of contact switches comprise a suite that provides multi-dimensional data about the user without the use of any type of camera or microphone equipment. Various physiological signals may be obtained to analyze the subject. Further, the data is preferably obtained completely by non-invasive technology, thereby allowing monitoring of the subject while reducing or eliminating an effect on the patient during the act of monitoring. By way of a specific example, a piezoelectric sensor, four of the temperature sensors and all the momentary contact switches may be sandwiched between two foam mattress pads. Four humidity sensors, four carbon dioxide sensors, two light sensors and potentially one of the piezoelectric sensors (if two are employed) may be embedded in a foam pillow. The type of foam used in the pillow may be a foam known as "memory foam." The actual mattress pad may be a sandwich of memory foam and high resilience foam. It may also employ a rubber sheet in between the two types of foam to provide necessary surface contact for the switches. This would make it compatible with any existing bed and allow the user to use standard sheets and pillowcases. The remaining two sensors, one carbon dioxide and one humidity sensor could be mounted on a swing arm that would be more ably attached to the headboard by conventional means. This arm may swing out over the person's head when the person is deemed asleep. As described above, one or more pressure switches in a pillow and/or the mattress may indicate the position of the subject, thereby allowing the swing arm to move as appropriate. Anytime the person lifts their head up the arm will retract so the person does not hit their head on the arm. If necessary, a fan may be employed to induce the surrounding airflow over the carbon dioxide and humidity sensors, which need to be calibrated against the ambient background levels.

According to another embodiment of the invention, an apparatus and method for the passive monitoring of physiological parameters such that sensors work together to acquire a multidimensional data set that can be interpreted to provide health diagnostic data or general health assessments includes various components. These components may include a vibration sensor for the sensitive detection of physiological characteristics including heart rate and breathing rate. The vibration sensor, in combination with the amplifiers and filters described above, may provide breathing and heart rate waveforms in a clear enough manner for an algorithm to interpret the waveforms and automatically provide heart rate and breathing rate information. For instance, heart rate waveform data can be interpreted to provide a measure of heart rate variability. An electromagnetic sensor may provide electromagnetic information about a subject. Also, by way of example, the process and apparatus may be used for detecting sleep apnea by examining the breathing waveform that flatline during a period of absence of respiration or multiple waveforms that show a pattern of paradoxical.

In addition, multiple instances of monitors that would obtain blood flow through various parts of the body (i.e., from chest to foot, neck to hand, etc.) may be used. The sensors would record pulse data and the time delay or phase shift between the two signals, thus providing the flow data or a measure that correlates with peripheral vascular resistance. By way of example, the process and apparatus may be used for obtaining a cuff-less blood pressure measurement interpreted from the flow rate data or from characteristics of the pulse waveforms such as area under the curve, rate of rise and change in magnitude of the contractile signals, rate of fall and change in magnitude of the dilation signal, ratio of contractile to dilation signal, and or pulse width. By way of an alternative example, the process and apparatus may be used in a mattress pad, block of foam or bed sheet that could be laid on top of a bed to provide pulse and breathing data during sleep. Alternatively, the process and apparatus may be used in a chair to monitor pulse and breathing rates during waking hours while the patient is sitting in a chair.

One application for which the invention as described above is particularly suitable is passive sleep monitoring. Having multiple piezoelectric sensor-pad combinations, one at the upper chest level and one at the abdomen level, provides a means to obtain multiple waveforms. The respiratory waveforms are generally out of phase during normal breathing and become in-phase during paradoxical breathing experienced when obstructive sleep apneas occur. Results have been obtained with the invention within five percent of accepted measurements of a pulse oximeter. Cardiac information is also pertinent to sleep architecture and quality. The system of the invention is able to examine the heart rate on a beat-by-beat basis, providing measures of heart rate, heart rate variability and blood pressure, all of which are key characteristics during sleep. Additionally, restlessness data from the movement artifact provides a general indication of sleep quality and comfort. The entire basic dataset (cardiac, respiratory, thermal and movement) provide a means of acquiring sleep staging, at the very least on a REM, non-REM level. This would be done through the use of analyzing all of these variables in lieu of attaching electrodes to monitor the person's brain waves through an electroencephalogram (EEG). Thus, the system of the invention looks at the results from the actions implemented by the brain rather than the actual brain waves themselves. Monitoring all of these parameters related to sleep in a longitudinal fashion, i.e., over a number of sleep cycles and/or days, can lead to a clearer picture of a person's sleep hygiene and architecture, including the effects on the quality of sleep and quantification of sleep quality. The system may be used in the subject's home, thus reducing a subject's discomfort. In addition, the system is capable of determining efficacy of treatment, since it is designed to monitor longitudinally.

Figure 12A:
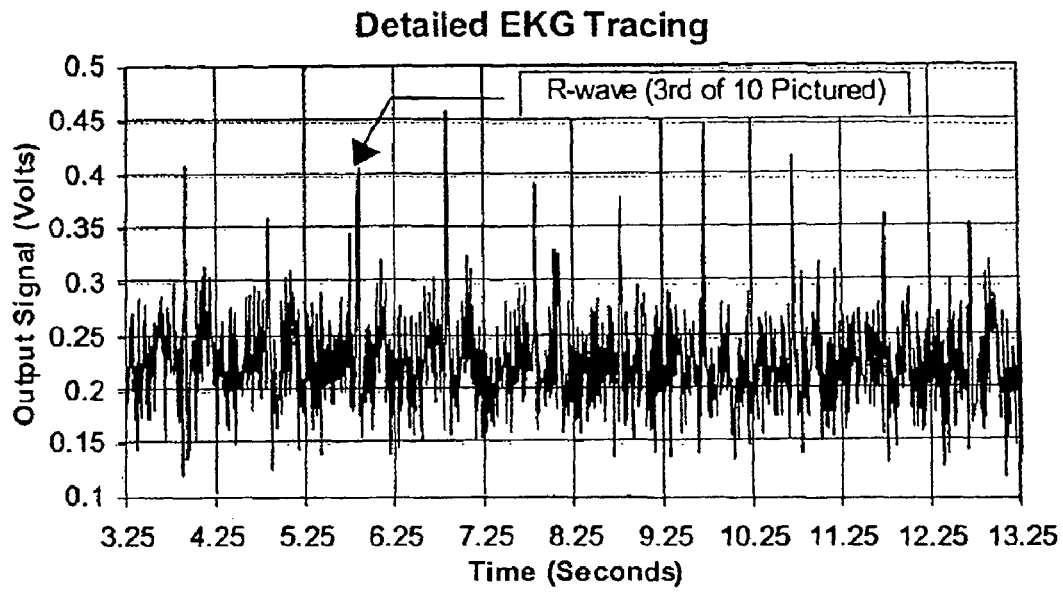
Figure 12B:
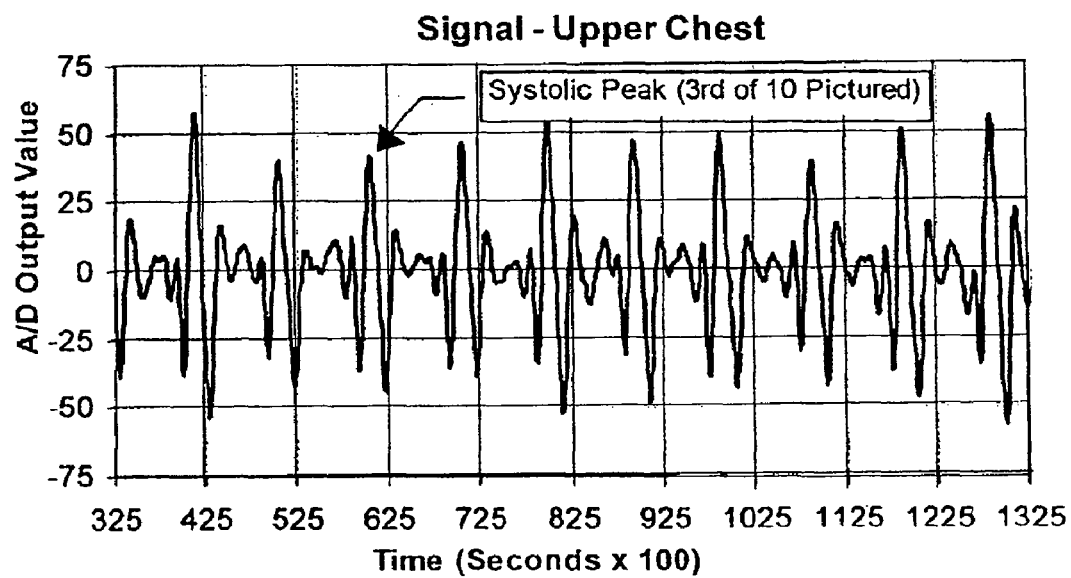
FIGS. 12B, 12C and 12D are sample waveforms, all obtained simultaneously using an EKG machine, or system for non-invasive analysis of physiological signals constructed according to the principles of the invention, respectively.
Figure 12C:
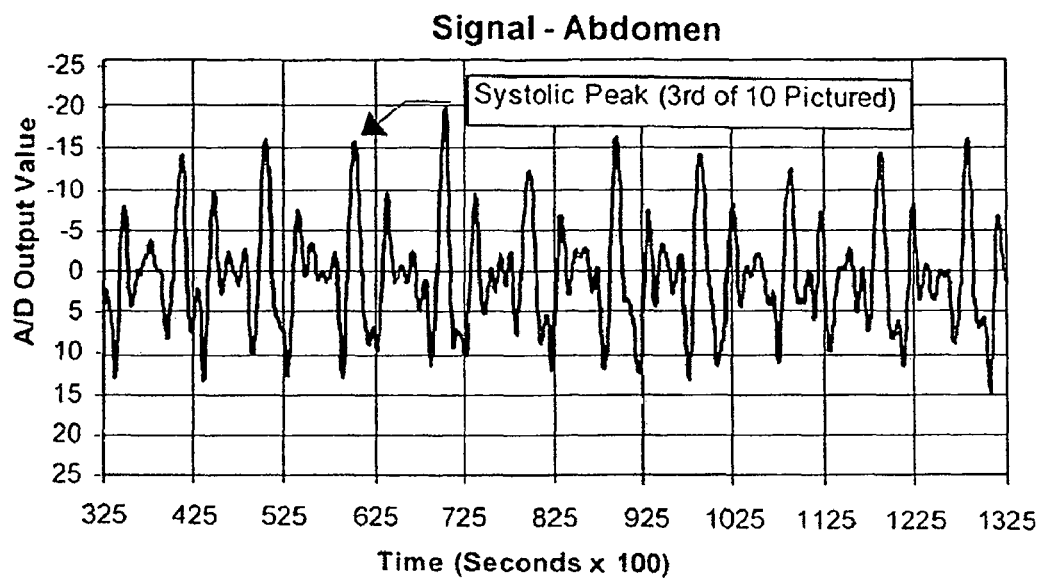
Figure 12D:
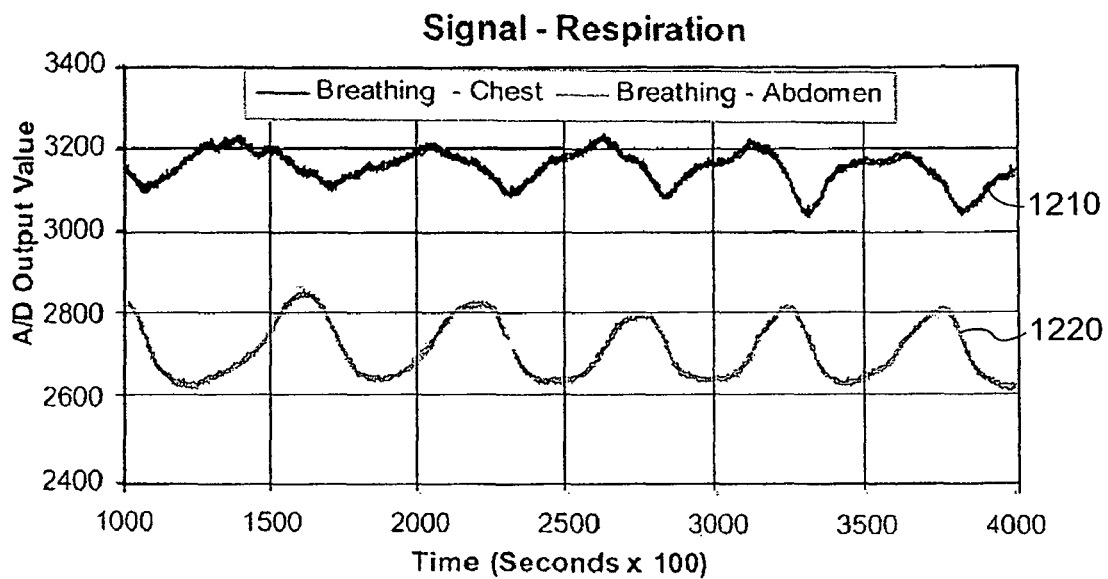

FIGS. 12B, 12C and 12D are sample waveforms obtained from a system for non-invasive analysis of physiological signals constructed according to the principles of the invention. A vibration pad sensor, such as vibration pad sensors 220 in FIG. 2, was placed at chest level on a subject and another vibration pad sensor was placed at abdomen level of the subject. The vibration pad sensors were foam pads with tubing at one end and a piezoelectric sensor at the other end of the tubing. The data from the vibration pad sensor was processed through a circuit similar to circuit 800 in FIG. 8.

FIG. 12A is an EKG waveform taken of the subject during the same time of the measurements that resulted in the sample waveforms of FIGS. 12B, 12C and 12D of the invention. FIG. 12B is a sample upper chest pulse waveform. FIG. 12C is a sample abdomen pulse waveform. The chest and abdomen pulse waveforms are compared to each other in an algorithm, such as that described in FIG. 14, so that if for some reason there is noise in one set, the other can be used. If both waveforms are good, they are compared to provide a more accurate assessment of heart rate. Ultimately, the best waveform is selected out of numerous processing techniques, so it provides added redundancy and reliability to enhance the accuracy and precision of the sensor. The "3rd of 10 pictured" systolic peak in FIGS. 12A, 1213, 12C refers to the fact that all three heart rate waveforms are displaying the same data set, meaning that the labeled peak is the same heartbeat in each of the figures, i.e., the waveforms represent the same data. Thus, the heart rate waveforms of the invention have comparable accuracy to that of conventional EKG readings.

FIG. 12D is a sample respiration waveform. The respiration waveform illustrates both breathing based on chest movement 1210 and breathing based on abdomen movement 1220. As can be seen by the example in FIG. 12D, the peak of the chest movement waveform 1210 is offset from the peak of the abdomen movement waveform 1220.

Figure 13A:
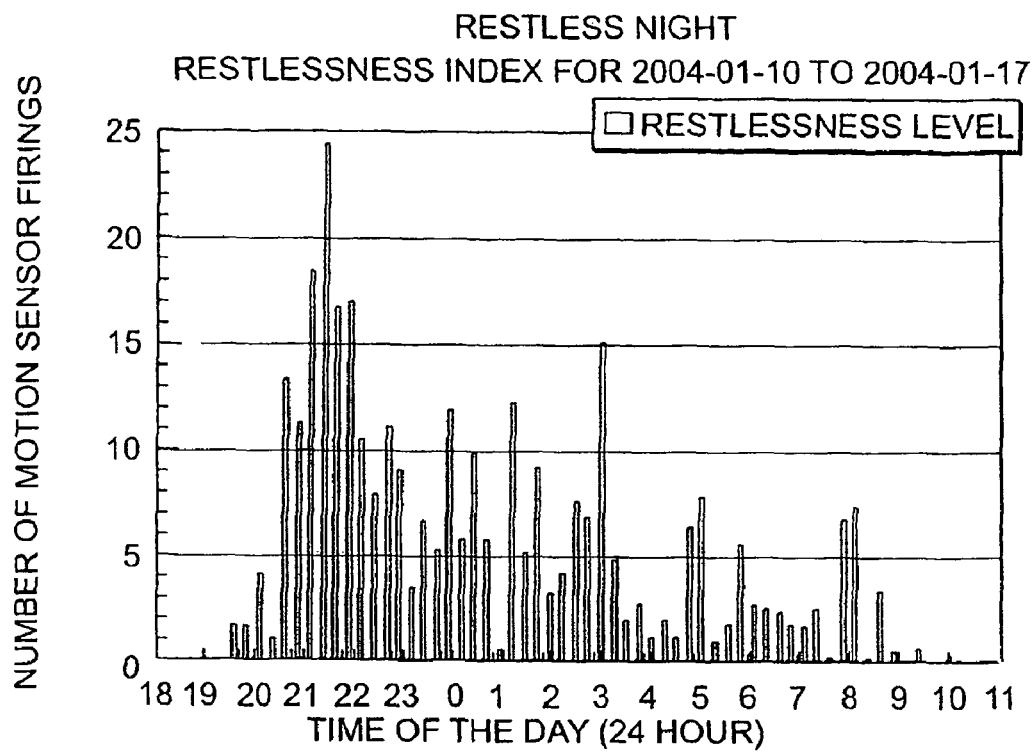
FIGS. 13A and 13B are graphs illustrating restlessness indexes based on information obtained from a non-invasive system constructed according to the invention.
Figure 13B:
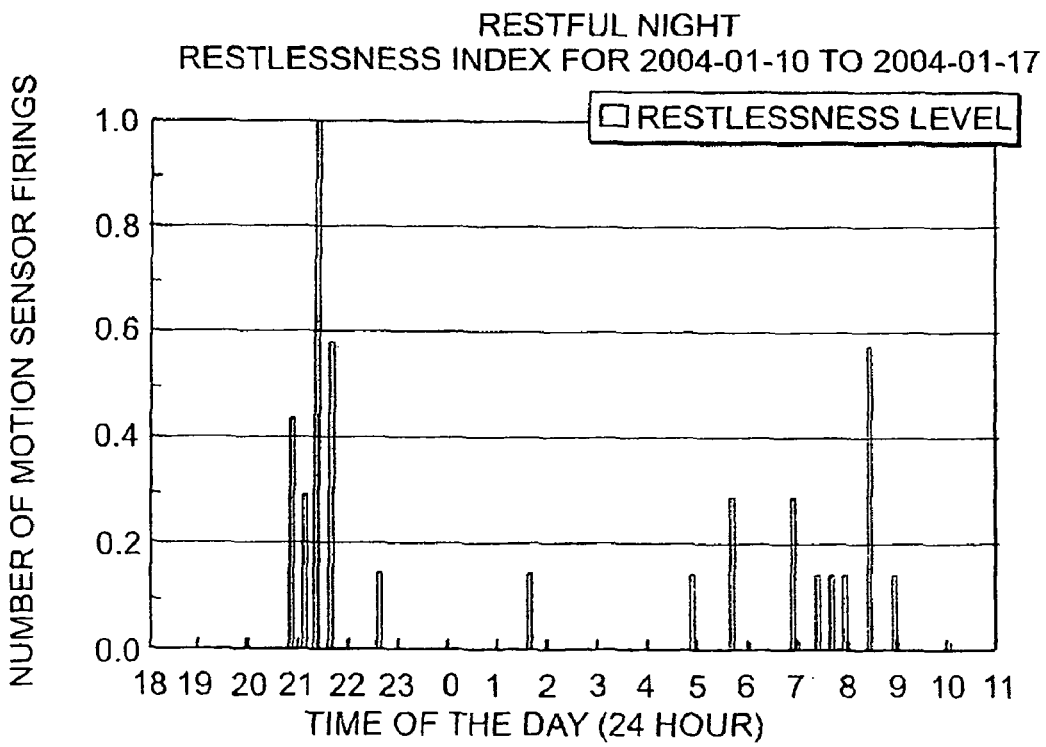

FIGS. 13A and 13B are graphs illustrating restlessness indexes based on information obtained from a non-invasive system constructed according to the invention. This data was taken using an embodiment of the invention using the circuit in FIG. 10 and taken from two different nights of sleep behavior of the subject. FIGS. 13A and 13B are bar graphs illustrating the number of movement sensor firings on the vertical axis and the time of day on the horizontal axis. FIG. 13A illustrates a relatively restless night's sleep, as there are a number of time periods with relatively large numbers of movement sensor firings. FIG. 13B illustrates a relatively restful night's sleep, as there are relatively few time periods with movement sensor firings. Further, there are time periods when no movement sensors fired.

Additionally, the movement artifact associated with the piezoelectric sensor provides a gauge of restlessness or activity while in contact with the sensors. Since the sensor is amplified to detect minute movement associated with cardiac events, gross body movements can be easily differentiated from cardiac or respiratory events, as the sensor voltage normally saturates, or clips, when movement occurs.

Graphs such as those shown in FIGS. 12B-12D, 13A and 13B may be used in combination to analyze the sleeping patterns of an individual. More specifically, heart rate, pulse waveforms, respiratory rate and restlessness information may provide information to allow the analysis of a subjects sleep patterns. Other analyses based on the information may also be performed.

Another application of the invention involves use in hospital beds. For patients that do not require close monitoring, the system may obtain vital signs and physiological characteristics without the need for the patient to have any instrumentation attached to his/her body. This would maximize the comfort of the patient while minimizing the intrusiveness. Providing this extra information could help caregivers maintain a well-informed view of patient's status or even alert them when they might be coming out of anesthesia. Since there is a documented fall risk for patients in hospitals, the passive monitoring of the invention provides automated alerts for patient activity so caregivers can be aware when patient's attempt to get up or move around. This way, they can provide assistance when needed before an accident may occur. One skilled in the art could see how this might apply to other situations in the hospital such as during or after hemodialysis treatments or other treatments that affect the cardiac or respiratory systems, or other environments.

Yet another application applies to bedridden individuals. Pressure ulcers are caused when a patient lies in one position for an extended period of time without being moved or shifting position. The system could provide vital information as to how much and what part of a patient has moved over a period of time. It could also indicate if there are particular pressure points that might be susceptible to the development of pressure bedsores. This would remove the burden of tracking how often a patient has moved off of the caregivers while automating and quantifying the process.

The disclosures of the following U.S. Patents and publications are incorporated by reference herein in their entirety: U.S. Pat. Nos. 6,342,039; 6,222,064; 5,891,023; 5,590,650; 4,163,447; 5,902,250; 5,335,657, 5,295,490; 4,306,657; Harada, T., Sato, T., Mori, T. "Estimation of Bed-Ridden Human's Gross and Slight Movement Based on Pressure Sensors Distribution Bed," The University of Tokyo; Alihanka, J., Vaahtoranta, K., Saarikivi, I., "A New Long-Term Monitoring of Ballistocardiogram, Heart Rate and Respiration," J. Physiol., Vol. 240, pp. 384-392, 1981; and Tamura, T., Togawa, T., Murata, M., "A Bed Temperature Monitoring System for Assessing Body Movement During Sleep," Clin. Phys., Physiol. Meas., 1988, Vol. 9, No. 2, pp. 139-45.

While the invention has been described in terms of exemplary embodiments, those skilled in the art will recognize that the invention can be practiced with modifications and in the spirit and scope of the appended claims. These examples given above are merely illustrative and are not meant to be an exhaustive list of all possible designs, embodiments, applications or modifications of the invention.

What is claimed is:

1. A non-invasive system for assessing physiological characteristics of a subject, said system comprising:
    a network of sensors configured to provide electronic output signals indicative of at least one sensed condition, said network including at least one passive sensor selected from the group consisting of vibration, temperature, carbon dioxide, humidity, electromagnetic and light sensors, and wherein said network of sensors further comprises a movable support including at least one sensor of the network of sensors;
    data acquisition circuitry for collecting the electronic signals output from said network of sensors;
    a processor configured to process the electronic signals, said processor including an amplifier configured to amplify at least one of the electronic signals, and first and second filters configured to receive the amplified electronic signals to produce two processed electronic signals, wherein said first filter includes a band pass filter and said second filter includes a low pass filter and a high pass filter, and wherein said first filter outputs a first signal corresponding to a respiratory rate on a breath-by-breath basis of the subject and said second filter outputs a second signal corresponding to a heart rate on a beat-by-beat basis of the subject; and
    an output device for outputting the processed signals into human-readable data indicative of at least one condition of a subject,
    wherein the human-readable data comprises a subject movement percentage.

2. The system of claim 1 wherein said system is adapted to assess the subject's quality of sleep and wherein:
    said data acquisition circuitry is configured to collect the electronic signals output from said network of sensors indicative of heart rate and/or respiratory rate;
    said first filter receives signals indicative of chest movement and said second filter receives signals indicative of heart movement; and
    said processor includes an algorithm to generate a heart rate and a respiratory rate based on processed electronic signals output at or below about 50 Hz.

3. The system of claim 2, further comprising an algorithm for determining sleep staging and aspects of sleep quality based on the heart rate, the respiratory rate, a variability of the heart rate, a variability of the respiratory rate and a subject movement percentage.

4. The system of claim 1, further comprising a microcontroller for converting the collected electronic signals into a bit stream to be logged into a data file for immediate analysis or for later review.

5. The system of claim 4, wherein said network of sensors includes at least one detector for sensing motion, the bit stream includes electronic signals from said at least detector and said processor processes the bit stream to provide a positional map of the subject.

6. The system of claim 1, wherein said amplifier comprises an instrumentation amplifier that provides buffering from said network of sensors and an infinite common mode rejection ratio.

7. The system of claim 1, wherein at least some of the sensors of the network of sensors are passive sensors requiring no active involvement from the subject and no direct attachment to the subject.

8. The system of claim 1, wherein human-readable data further comprises at least one of a heart rate waveform and a respiratory waveform.

9. The system of claim 1, wherein the human-readable data further comprises an obstructive sleep apnea count.

10. The system of claim 1, wherein at least part of the system is incorporated in one of a mattress pad or pillow, a bed or chair at a sleep lab, a bed or chair at an elder care facility, a bed or chair at a hospital for children or adults, a bed or baby support at a prenatal care facility, and a publicly available health monitoring station.

11. The system of claim 1, wherein said data acquisition circuitry further comprises a user activated privacy flag to flag for omission output signals from said network of sensors.

12. The system of claim 1, wherein said network of sensors can saturate when gross movement occurs.

13. The system of claim 12, wherein the saturation of said network of sensors allows differentiation between gross movement and acute movements.

14. The system of claim 13, wherein gross movement includes physical repositioning and acute movement includes cardiac and respiratory events.

15. The system of claim 14, wherein at least one of the gross movement and acute movement are interpreted to prevent development of pressure ulcers or bed sores in the patient.

16. The system of claim 1, wherein said sensors are from the group including piezoelectric, fiber optic, or load cell.

17. A non-invasive system for assessing physiological characteristics of a subject, said system comprising:
    a network of sensors configured to provide electronic output signals indicative of at least one sensed condition, said network including at least one passive sensor selected from the group consisting of vibration, temperature, carbon dioxide, humidity, electromagnetic and light sensors;
    data acquisition circuitry for collecting the electronic signals output from said network of sensors, said circuitry including a user activated privacy flag to flag for omission output signals from said network of sensors;
    a processor configured to process the electronic signals, said processor including an amplifier configured to amplify at least one of the electronic signals, and first and second filters configured to receive the amplified electronic signals to produce two processed electronic signals, wherein said first filter includes a band pass filter and said second filter includes a low pass filter and a high pass filter, and wherein said first filter outputs a first signal corresponding to a respiratory rate on a breath-by-breath basis of the subject and said second filter outputs a second signal corresponding to a heart rate on a beat-by-beat basis of the subject; and
    an output device for outputting the processed signals into human-readable data indicative of at least one condition of a subject,
    wherein the human-readable data comprises a subject movement percentage.

18. A non-invasive system for assessing physiological characteristics of a subject, said system comprising:
- a network of sensors configured to provide electronic output signals indicative of at least one sensed condition, said network including at least one passive sensor selected from the group consisting of vibration, temperature, carbon dioxide, humidity, electromagnetic and light sensors, wherein said network of sensors can saturate when gross movement occurs;
- data acquisition circuitry for collecting the electronic signals output from said network of sensors;
- a processor configured to process the electronic signals, said processor including an amplifier configured to amplify at least one of the electronic signals, and first and second filters configured to receive the amplified electronic signals to produce two processed electronic signals, wherein said first filter includes a band pass filter and said second filter includes a low pass filter and a high pass filter, and wherein said first filter outputs a first signal corresponding to a respiratory rate on a breath-by-breath basis of the subject and said second filter outputs a second signal corresponding to a heart rate on a beat-by-beat basis of the subject; and
- an output device for outputting the processed signals into human-readable data indicative of at least one condition of a subject,
- wherein the human-readable data comprises a subject movement percentage.

19. The system of claim 18, wherein saturation of said sensors allows differentiation between gross movement and acute movements.

20. A non-invasive system for assessing physiological characteristics of a subject, said system comprising:
- a network of sensors configured to provide electronic output signals indicative of at least one sensed condition, said network including at least one passive sensor selected from the group consisting of vibration, temperature, carbon dioxide, humidity, electromagnetic and light sensors, and wherein said network of sensors further comprises a movable support including at least one sensor of the network of sensors;
- data acquisition circuitry for collecting the electronic signals output from said network of sensors;
- a processor configured to process the electronic signals, said processor including an amplifier configured to amplify at least one of the electronic signals, and first and second filters configured to receive the amplified electronic signals to produce two processed electronic signals, wherein said first filter includes a band pass filter and said second filter includes a low pass filter and a high pass filter, and wherein said first filter outputs a first signal corresponding to a respiratory rate on a breath-by-breath basis of the subject and said second filter outputs a second signal corresponding to a heart rate on a beat-by-beat basis of the subject; and
- an output device for outputting the processed signals into human-readable data indicative of at least one condition of a subject,
- wherein said system is adapted to assess the subject's quality of sleep and wherein:
- said data acquisition circuitry is configured to collect the electronic signals output from said network of sensors indicative of heart rate and/or respiratory rate;
- said first filter receives signals indicative of chest movement and said second filter receives signals indicative of heart movement; and
- said processor includes an algorithm to generate a heart rate and a respiratory rate based on processed electronic signals output at or below about 50 Hz, and an algorithm for determining sleep staging and aspects of sleep quality based on the heart rate, the respiratory rate, a variability of the heart rate, a variability of the respiratory rate and a subject movement percentage.

* * * * *